United States Patent
Acharya et al.

(10) Patent No.: US 12,144,836 B2
(45) Date of Patent: Nov. 19, 2024

(54) PROBIOTICS AND PROBIOTIC COMPOSITIONS FOR REGULATING BODY WEIGHT

(71) Applicant: UNIVERSITY OF PITTSBURGH—OF THE COMMONWEALTH SYSTEM OF HIGHER EDUCATION, Pittsburgh, PA (US)

(72) Inventors: Abhinav Prakash Acharya, Pittsburgh, PA (US); Steven R. Little, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 0 days.

(21) Appl. No.: 18/122,835

(22) Filed: Mar. 17, 2023

(65) Prior Publication Data
US 2023/0210918 A1    Jul. 6, 2023

Related U.S. Application Data

(63) Continuation of application No. 17/005,217, filed on Aug. 27, 2020, now Pat. No. 11,638,727, which is a continuation of application No. PCT/US2019/019845, filed on Feb. 27, 2019.

(60) Provisional application No. 62/635,753, filed on Feb. 27, 2018.

(51) Int. Cl.
| | |
|---|---|
| A61K 35/741 | (2015.01) |
| A23L 33/135 | (2016.01) |
| A61K 35/00 | (2006.01) |
| A61K 35/744 | (2015.01) |
| A61P 3/04 | (2006.01) |

(52) U.S. Cl.
CPC .......... *A61K 35/741* (2013.01); *A23L 33/135* (2016.08); *A61K 35/744* (2013.01); *A61P 3/04* (2018.01); *A23V 2400/245* (2023.08); *A61K 2035/115* (2013.01)

(58) Field of Classification Search
None
See application file for complete search history.

(56) References Cited

U.S. PATENT DOCUMENTS

| | | |
|---|---|---|
| 9,113,641 B2 | 8/2015 | Arulampalam et al. |
| 2012/0027736 A1 | 2/2012 | Morita et al. |
| 2013/0121968 A1 | 5/2013 | Quay |
| 2016/0113972 A1 | 4/2016 | Bjorck et al. |
| 2020/0056145 A1* | 2/2020 | Brown .................... C12N 1/20 |

FOREIGN PATENT DOCUMENTS

WO    WO 2018/022327 A1    2/2018

OTHER PUBLICATIONS

U.S. Appl. No. 17/410,360 (US 2021/0379121), filed Aug. 24, 2021 (Dec. 9, 2021).
U.S. Appl. No. 17/410,360, Aug. 2, 2023 Non-Final Office Action.
Ryan et al., "Screening for and Identification of Starch-, Amylopectin-, and Pellulan-Degrading Activities in Bifidobacterial Strains," Applied and Environmental Microbiology 72(8):5289-5296 (2006).
Stephen Daniells, "Probiotics may influence carbohydrate metabolism: 'Elegant' study," NutraIngredients, USA (Oct. 27, 2011).
U.S. Appl. No. 17/005,217 (U.S. Pat. No. 11,638,727), filed Aug. 27, 2020 (May 2, 2023).
U.S. Appl. No. 17/005,217, Mar. 17, 2023 Issue Fee Payment.
U.S. Appl. No. 17/005,217, Jan. 6, 2023 Notice of Allowance.
U.S. Appl. No. 17/005,217, Dec. 21, 2022 Notice of Allowance.
U.S. Appl. No. 17/005,217, Nov. 30, 2022 Response After Final Action.
U.S. Appl. No. 17/005,217, filed Sep. 30, 2022 Final Office Action.
U.S. Appl. No. 17/005,217, filed Sep. 12, 2022 Response to Non-Final Office Action.
U.S. Appl. No. 17/005,217, filed May 18, 2022 Non-Final Office Action.
U.S. Appl. No. 17/005,217, filed Jan. 28, 2022 Response to Non-Final Office Action.
U.S. Appl. No. 17/005,217, filed Nov. 8, 2021 Non-Final Office Action.
U.S. Appl. No. 17/005,217, filed Aug. 6, 2021 Response to Restriction Requirement.
U.S. Appl. No. 17/005,217, filed Jul. 9, 2021 Restriction Requirement.
Borgeraas et al., "Effects of probiotics on body weight, body mass index, fat mass and fat percentage in subjects with overweight or obesity: a systematic review and meta-analysis of randomized controlled trials," Obes Rev. 19:219-232 (2018).
Ding et al., "An improved method of microencapsulation of probiotic bacteria for their stability in acidic and bile conditions during storage," J. Food Sci. 74(2):M53-M61 (2009).

(Continued)

*Primary Examiner* — S. Devi
(74) *Attorney, Agent, or Firm* — Baker Botts L.L.P.

(57) ABSTRACT

The present disclosure relates to probiotics and probiotic compositions having modified energy metabolisms (e.g., modifying, metabolizing, or storing energy molecules, e.g., lipids, before the energy molecules are absorbed by a host subject), and thus modulating the absorption of the energy molecules by the host subject. The present disclosure also relates to methods of making such probiotics and probiotic compositions. The present disclosure further relates to methods of regulating (e.g., maintaining or reducing) body weight in a subject (e.g., a subject having a healthy BMI, a subject having an overweight BMI, a subject having an obese BMI), using the probiotics and probiotic compositions disclosed herein.

15 Claims, 16 Drawing Sheets

(56) References Cited

OTHER PUBLICATIONS

Ding et al., "Effect of various encapsulating materials on the stability of probiotic bacteria," J. Food Sci. 74(2):M100-M107 (2009).
Flegal et al., "Prevalence and trends in obesity among US adults, 1999-2008," JAMA 303(3):235-241 (2010).
Hamad et al., "Milk fermented by Lactobacillus gasseri SBT2055 influences adipocyte size via inhibition of dietary fat absorption in Zucker rats," Br. J. Nutr. 101(5):716-724 (2009).
International Search Report and Written Opinion dated Apr. 30, 2019 in International Application No. PCT/US2019/019845.
Jung et al., "Effect of Lactobacillus gasseri BNR17 on Overweight and Obese Adults: A Randomized, Double-Blind Clinical Trial," Korean J. Fam. Med. 34(2):80-89 (2013).
Kang et al., "Anti-Obesity Effect of Lactobacillus gasseri BNR17 in High-Sucrose Diet-Induced Obese Mice," PLoS One 8(1):e54617 (2013).
Kau et al., "Human nutrition, the gut microbiome and the immune system," Nature 474(7351):327-336 (2011).
Lee et al., "Bacterial colonization factors control specificity and stability of the gut microbiota," Nature, 501(7467):426-429 (2013).
Lim et al., "A comparative risk assessment of burden of disease and injury attributable to 67 risk factors and risk factor clusters in 21 regions, 1990-2010: a systematic analysis for the Global Burden of Disease Study 2010," Lancet 380:2224-2260 (2012).
Ng et al., "Global, regional, and national prevalence of overweight and obesity in children and adults during 1980-2013: a systematic analysis for the Global Burden of Disease Study 2013," Lancet 384:766-781 (2014).
Park et al., "Multiple-unit tablet of probiotic bacteria for improved storage stability, acid tolerability, and in vivo intestinal protective effect," Drug Des. Devel. Ther. 10:1355-1364 (2016).
Phalipon et al., "Secretory component: a new role in secretory IgA-mediated immune exclusion in vivo," Immunity, 17:107-115 (2002).
Savini et al., "Pilot-scale production and viability analysis of freeze-dried probiotic bacteria using different protective agents," Nutrients 2:330-339 (2010).
Semova et al., "Microbiota regulate intestinal absorption and metabolism of fatty acids in the zebrafish," Cell Host & Microbe, 12(3):277-288 (2012).
Yatsunenko et al., "Human gut microbiome viewed across age and geography," Nature 486:222-227 (2012).
U.S. Appl. No. 17/410,360, Feb. 26, 2024 Final Office Action.
Ibrahim et al., "Use of Chemical Mutagenesis for the Isolation of Food Grade β-Galactosidase Overproducing Mutants of Bifidobacteria, Lactobacilli and *Streptococcus thermophilus*," Journal of Dairy Science 83(5):923-930 (2000).
U.S. Appl. No. 17/410,360, filed Aug. 5, 2024 Non-Final Office Action.
News Desk, Would you like to supersize your gut bacteria with that?, Mar. 23, 2016, 1 page.
Sarian et al., "Enzymatic degradation of granular potato starch by Microbacterium aurum strain B8. A," Applied Microbiology and Biotechnology 93:645-654 (2012).
Valk et al., "Characterization of the starch-acting MaAmyB enzyme from Microbacterium aurum B8. A representing the novel subfamily GH13_42 with an unusual, multi-domain organization," Scientific Reports 6:36100 (2016) 12 pgs.
Valk et al., "Degradation of Granular Starch by the Bacterium Microbacterium aurum Strain B8. A Involves a Modular a-Amylase Enzyme System with FNIII and CBM25 Domains," Applied and Environmental Microbiology 81(19):6610-6620 (2015).

* cited by examiner

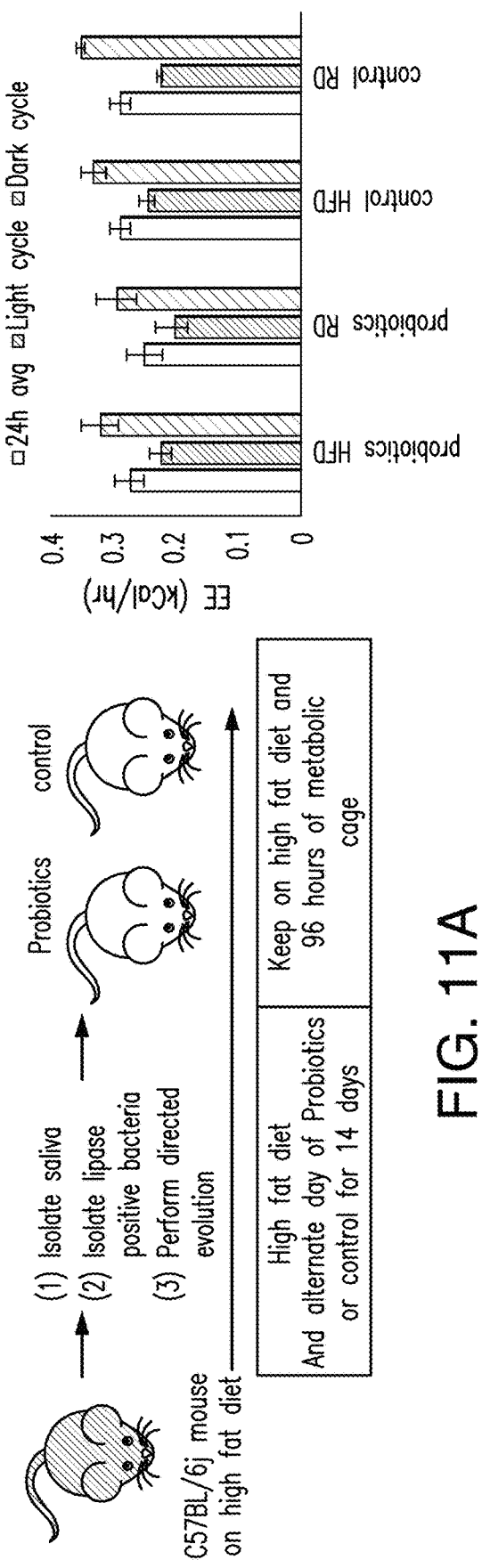
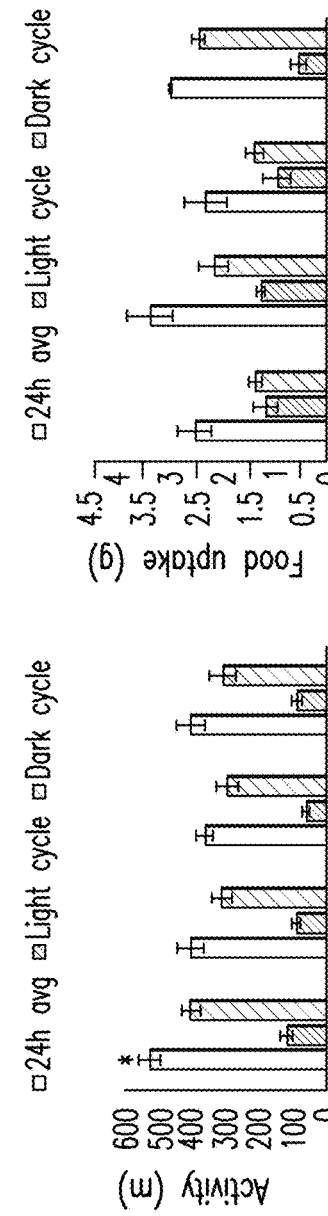
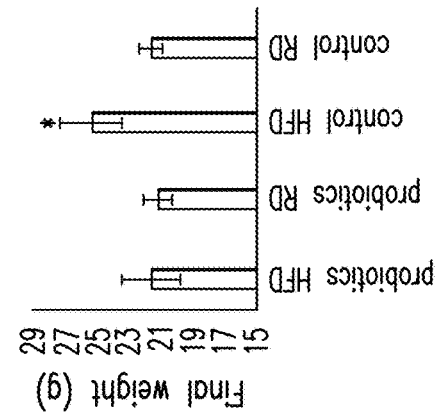
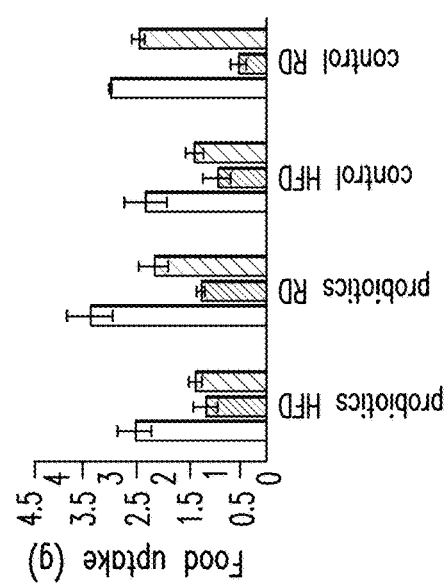
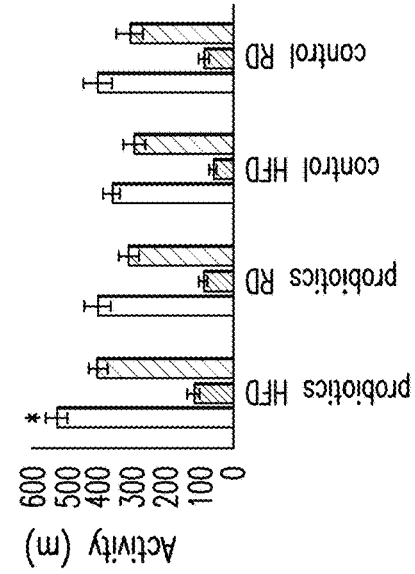
FIG. 11A
FIG. 11B
FIG. 11C
FIG. 11D
FIG. 11E

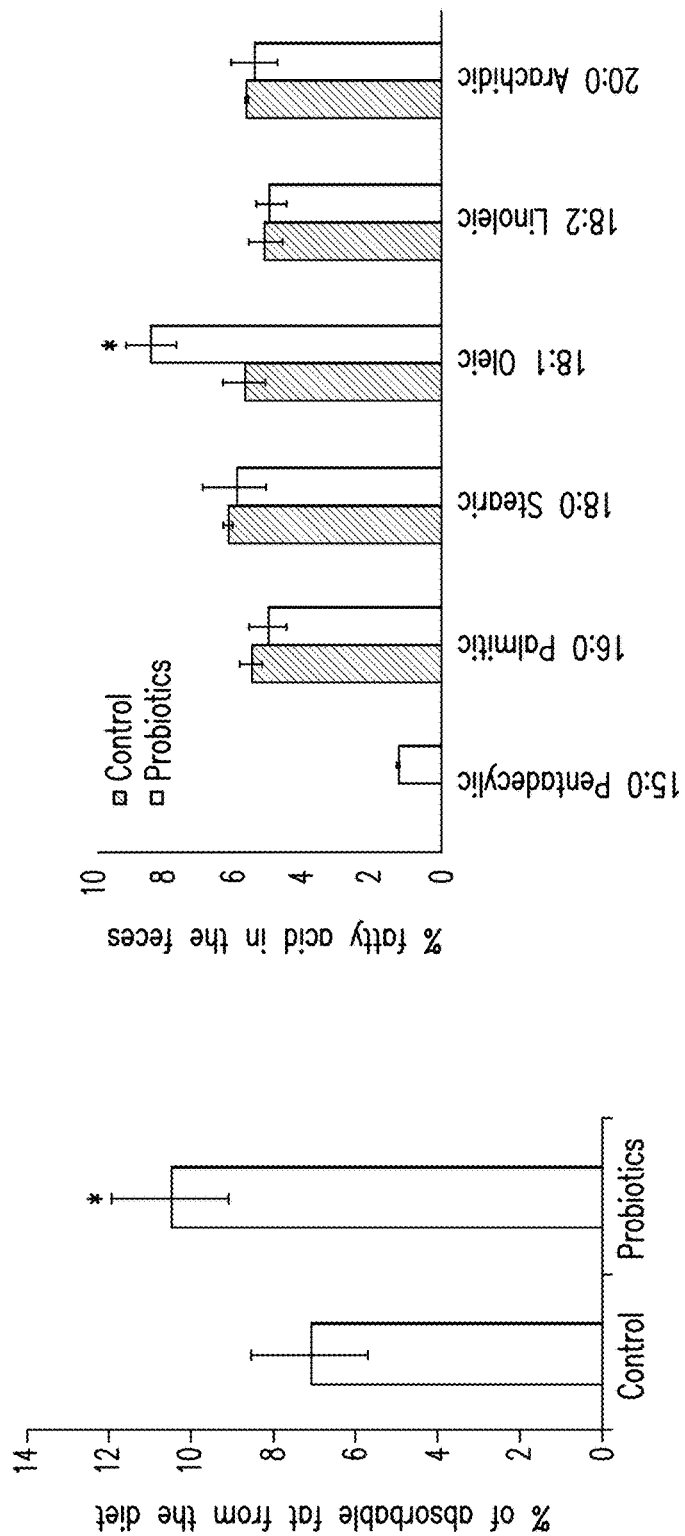
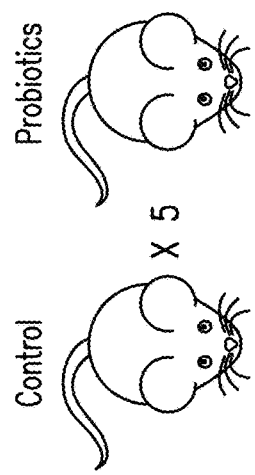
FIG. 14A
FIG. 14B
FIG. 14C

PROBIOTICS AND PROBIOTIC COMPOSITIONS FOR REGULATING BODY WEIGHT

CROSS-REFERENCE TO RELATED APPLICATIONS

This application is a continuation of U.S. application Ser. No. 17/005,217, filed on Aug. 27, 2020, now U.S. Pat. No. 11,638,727, issued on May 2, 2023, which is a continuation of International Patent Application No. PCT/US2019/019845, filed on Feb. 27, 2019, which claims priority to U.S. Provisional Application No. 62/635,753, filed on Feb. 27, 2018, the contents of each of which are hereby incorporated by reference in their entireties, and to each of which priority is claimed.

1. INTRODUCTION

The present disclosure relates to probiotics and probiotic compositions having modified energy metabolisms (e.g., modifying, metabolizing, or storing energy molecules, e.g., lipids, before the energy molecules are absorbed by a host subject), and thus regulating the absorption of the energy molecules by the host subject. The present disclosure also relates to methods of making such probiotics and probiotic compositions. The present disclosure further relates to methods of regulating (e.g., maintaining or reducing) body weight in a subject (e.g., a subject having a healthy body mass index (BMI), a subject having an overweight BMI, a subject having an obese BMI), using the probiotics and probiotic compositions disclosed herein.

2. BACKGROUND OF THE INVENTION

Obesity has reached epidemic proportions worldwide, with 36.9% of men and 29.8% of women considered either overweight (body mass index (BMI) 25-29.9 kg m$^{-2}$) or obese (BMI≥30 kg m$^{-2}$).[1] Importantly, there is a rise in childhood obesity with more than 17 million children under 5 years of age obese worldwide. Obesity has been linked to different disorders such as type 2 diabetes, cardiovascular disease, hypertension, stroke and certain forms of cancer (FIG. 1).[2] The consequences of these disorders include increased risk of premature death and severely reduced overall quality of life.

Reasons for this global obesity epidemic include, for example urbanized diets that have shifted towards increased proportions of fats, saturated fats, and sugars. Recommended treatments for obesity and overweight include dietary therapy, physical therapy, pharmacotherapy, and surgery. Despite these treatments, widespread and consistent increase in number of overweight and obese persons have been observed over the past few decades, partly due to the diverse lifestyles of people in different regions of the world.[3]

Therefore, there remains a need for interventions for effectively preventing and treating overweight and obesity.

3. SUMMARY OF THE INVENTION

The present disclosure relates to probiotics and probiotic compositions having modified energy metabolisms, e.g., modifying, metabolizing, or storing energy molecules (e.g., lipids) before the energy molecules are absorbed by a host subject. Thus, the probiotics and probiotic compositions disclosed herein can regulate the absorption of the energy molecules by the host subject, e.g. at the gastrointestinal tract e.g., intestines, e.g., small intestine. The present disclosure further relates to methods of regulating (e.g., maintaining or reducing) body weight in a subject, or treating a subject suffering from overweight or obesity, using the probiotics and probiotic compositions disclosed herein.

The present disclosure also relates to methods of making such probiotics and probiotic compositions.

In one aspect, the present disclosure provides a method of making a probiotic composition for treating an overweight subject including obtaining a microbiota sample from a subject, isolating bacteria from the microbiota sample, developing probiotic bacteria having modified metabolism by subjecting the isolated bacteria to a stress-based directed evolution, compared to isolated bacteria not subject to the stress-based directed evolution; and including the probiotic bacteria having modified metabolism in the probiotic composition.

In another aspect, the present disclosure provides a method of making a probiotic composition for treating an overweight subject including obtaining a microbiota sample from a subject, isolating bacteria from the microbiota sample, developing probiotic bacteria that utilize lipids as a source of energy by subjecting the isolated bacteria to a stress-based directed evolution; and including the probiotic bacteria having lipid metabolism in the probiotic composition.

In yet another aspect, the present disclosure provides a method of making a probiotic composition for treating an overweight subject including obtaining a microbiota sample from a subject, isolating bacteria from the microbiota sample, subjecting the isolated bacteria to a stress-based directed evolution to develop probiotic bacteria having increased metabolism as compared to the isolated bacteria that are not subject to stress-based directed evolution; and including the probiotic bacteria having increased metabolism in the probiotic composition.

In yet another aspect, the present disclosure provides a method of making a probiotic composition comprising: (a) obtaining a microbiota sample from a subject: (b) isolating bacteria from the microbiota sample: (c) subjecting the isolated bacteria to a stress-based directed evolution to generate the probiotic bacteria, wherein the probiotic bacteria have a modified metabolism as compared to the isolated bacteria obtained in step (b); and (d) incorporating the probiotic bacteria to the probiotic composition.

In yet another aspect, the present disclosure provides a method of making a probiotic composition comprising: (a) obtaining a microbiota sample from the subject; (b) isolating bacteria from the microbiota sample: (c) selecting probiotic bacteria from the isolated bacteria, wherein the probiotic bacteria have a modified metabolism as compared to the isolated bacteria obtained in step (b): (d) growing the probiotic bacteria to obtain an effective amount of the probiotic bacteria; and (e) incorporating the effective amount of the probiotic bacteria to the probiotic composition.

In certain embodiments, a probiotic composition comprises an effective amount of the probiotic bacteria disclosed herein and an acceptable carrier.

In certain embodiments, the probiotic composition further comprises one or more anti-obesity agents.

In yet another aspect, the present disclosure provides a method for treating an overweight or an obese subject including obtaining a microbiota sample from the subject, isolating bacteria from the microbiota sample, developing probiotic bacteria having modified metabolism by subjecting the isolated bacteria to a stress-based directed evolution;

and administering to the subject an effective amount of the probiotic bacteria having modified metabolism. In certain embodiments, the probiotic bacteria having modified metabolism utilize lipids as a source of energy.

In yet another aspect, the present disclosure provides a method for treating an overweight or an obese subject, including obtaining a microbiota sample from the subject, isolating bacteria from the microbiota sample, selecting, from the isolated bacteria, the bacteria having modified metabolism, culturing the isolated bacteria having modified metabolism to obtain an effective amount of the bacteria, and administering to the subject an effective amount of the bacteria having modified metabolism.

In yet another aspect, the present disclosure provides a method of inhibiting or reducing a lipid absorption in a gastrointestinal tract of a subject comprising: (a) obtaining a microbiota sample: (b) isolating bacteria from the microbiota sample: (c) subjecting the isolated bacteria to a stress-based directed evolution to generate probiotic bacteria, wherein the probiotic bacteria have a modified lipid metabolism as compared to the isolated bacteria obtained from step (b); and (d) administering to the subject an effective amount of the probiotic bacteria, wherein the probiotic bacteria inhibit or reduce an amount of lipids that is available for absorption in the gastrointestinal tract of the subject.

In one aspect, the present disclosure provides a method for regulating body weight of a subject comprising: (a) obtaining probiotic bacteria, wherein the probiotic bacteria have a lipid metabolism; and (b) administering to the subject an effective amount of the probiotic bacteria.

In another aspect, the present disclosure provides a method of regulating body weight of a subject comprising: (a) obtaining probiotic bacteria, wherein the probiotic bacteria have a lipid metabolism: (b) subjecting the probiotic bacteria obtained in step (a) to a stress-based directed evolution to generate probiotic bacteria having an increased lipid metabolism as compared to the probiotic bacteria obtained in step (a); and (c) administering to the subject an effective amount of the probiotic bacteria having the increased lipid metabolism.

In certain embodiments, the microbiota sample is a saliva sample or a stool sample. In certain embodiments, the modified metabolism is a modified lipid metabolism. In certain embodiments, the modified lipid metabolism is a modified fatty acid metabolism. In certain embodiments, the probiotic bacteria have a modified lipase activity.

In certain embodiments, the probiotic bacteria utilize lipids as a source of energy. In certain embodiments, the probiotic bacteria reduce a lipid absorption by the subject. In certain embodiments, the probiotic bacteria decrease the amount of lipids available for absorption by the subject. In certain embodiments, the probiotic bacteria survive in a culture media comprising at least about 60%, at least about 70%, at least about 80%, at least about 90%, at least about 95%, at least about 99%, or at least about 100% v/v lipids. In certain embodiments, the stress-based directed evolution comprises culturing the isolated bacteria in increasing lipid concentrations.

In another aspect, the present disclosure provides a method of regulating body weight of a subject, comprising: (a) obtaining a microbiota sample: (b) isolating bacteria from the microbiota sample: (c) subjecting the isolated bacteria to a stress-based directed evolution to generate probiotic bacteria, wherein the probiotic bacteria have a modified metabolism as compared to the isolated bacteria obtained in step (b); and (d) administering to the subject an effective amount of the probiotic bacteria.

In one aspect, the present disclosure provides a method of regulating body weight of a subject, comprising: (a) obtaining a microbiota sample: (b) isolating bacteria from the microbiota sample: (c) selecting probiotic bacteria from the isolated bacteria, wherein the probiotic bacteria have a modified metabolism as compared to the isolated bacteria obtained in step (b): (d) growing the probiotic bacteria to obtain an effective amount of the probiotic bacteria; and (e) administering to the subject the effective amount of the probiotic bacteria.

In certain embodiments, the method maintains the body weight of the subject. In certain embodiments, the method reduces the body weight of the subject.

In certain embodiments, the subject has a healthy BMI. In certain embodiments, the subject has an overweight BMI. In certain embodiments, the subject is obese or has an obese BMI.

In certain embodiments, the microbiota sample is a saliva sample or a stool sample. In certain embodiments, the microbiota sample is obtained from the subject.

In certain embodiments, the modified metabolism is a modified lipid metabolism. In certain embodiments, the modified lipid metabolism is a modified fatty acid metabolism. In certain embodiments, the probiotic bacteria have a modified lipase activity. In certain embodiments, the probiotic bacteria utilize lipids as a source of energy. In certain embodiments, the probiotic bacteria reduces a lipid absorption by the subject. In certain embodiments, the probiotic bacteria decrease the amount of lipids available for absorption by the subject.

In certain embodiments, the probiotic bacteria survive in a culture media comprising at least about 60%, at least about 70%, at least about 80%, at least about 90%, at least about 95%, at least about 99%, or at least about 100% v/v lipids. In certain embodiments, the stress-based directed evolution comprises culturing the isolated bacteria or probiotic bacteria in increasing lipid concentrations.

In yet another aspect, the present disclosure provides a probiotic composition comprising probiotic bacteria, wherein the probiotic bacteria have a modified metabolism.

In certain embodiments, the probiotic composition is for use in regulating a body weight of a subject. In certain embodiments, the probiotic composition is for use in maintaining or reducing the body weight of the subject. In certain embodiments, the subject has a healthy BMI, an overweight BMI, or an obese BMI. In certain embodiments, the probiotic composition is for use in treating an obese or overweight subject. In certain embodiments, the probiotic composition comprises an effective amount of the probiotic bacteria.

In certain embodiments, the modified metabolism is a modified lipid metabolism. In certain embodiments, the modified lipid metabolism is a modified fatty acid metabolism. In certain embodiments, the probiotic bacteria have a modified lipase activity. In certain embodiments, the probiotic bacteria have an increased lipid metabolism as compared to isolated bacteria that are not subject to stress-based directed evolution, wherein the isolated bacteria are isolated from a microbiota sample from a subject. In certain embodiments, the probiotic bacteria have an increased fatty acid metabolism as compared to isolated bacteria that are not subject to stress-based directed evolution, wherein the isolated bacteria are isolated from a microbiota sample from a subject. In certain embodiments, the probiotic bacteria have an increased lipase activity as compared to isolated bacteria that are not subject to stress-based directed evolution, wherein the isolated bacteria are isolated from a microbiota sample from a subject.

In certain embodiments, the probiotic bacteria reduce a lipid absorption by the subject. In certain embodiments, the probiotic bacteria survive in a culture media comprising at least about 60%, at least about 70%, at least about 80%, at least about 90%, at least about 95%, at least about 99%, or at least about 100% v/v lipids.

In certain embodiments, the probiotic composition further comprises an acceptable carrier. In certain embodiments, the probiotic composition further comprises one or more anti-obesity agent.

In certain embodiments, the probiotic bacteria having an increased lipid metabolism as compared to isolated bacteria that are not subject to stress-based directed evolution and/or the probiotic bacteria that utilize lipids as a source of energy, inhibit lipid absorption by the subject by actively reducing the amount of lipids available for absorption by the subject.

In another aspect, the presently disclosure relates to kits including an effective amount of a probiotic composition disclosed herein. In certain embodiments, the kits further comprise one or more anti-obesity agents. In certain embodiments, the kits further comprise one or more weight management agents.

4. BRIEF DESCRIPTION OF THE FIGURES

Figure 4:
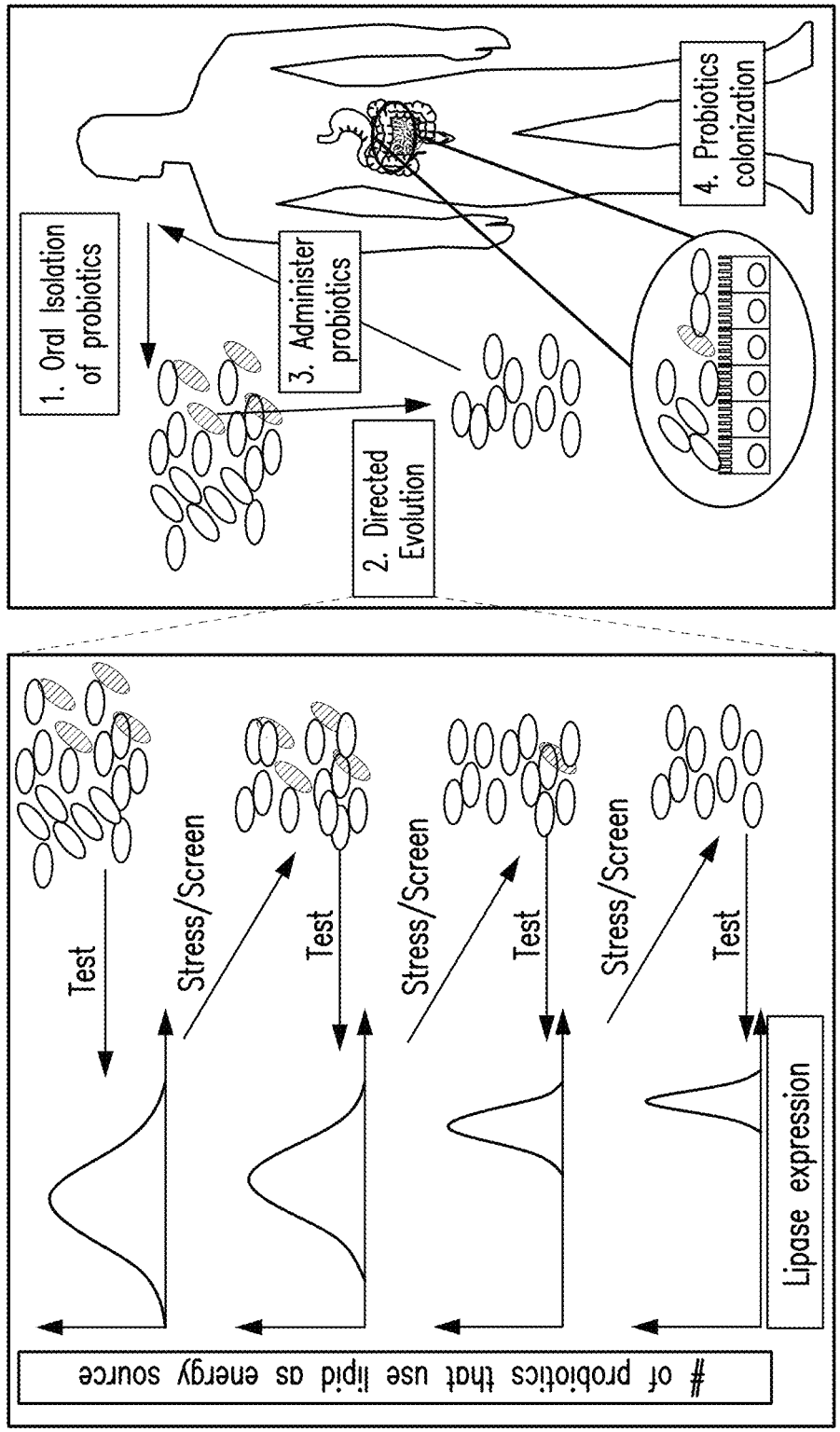

FIG. 4 shows the strategy to obtain probiotics of the disclosed subject matter. 1. Probiotics are isolated from the subject. 2. These probiotics undergo stress-based directed evolution. Stress-based directed evolution steps of repeated stress, screening and test are performed to isolate probiotics that have increased lipase expression and lipid metabolism, compared to isolated bacteria that were not subject to stress-based directed evolution. 3. After stress-based directed evolution, the probiotics can be administered back to the subject. 4. These probiotics can have a higher chance of colonizing the gastrointestinal (GI) tract.

Figure 5:
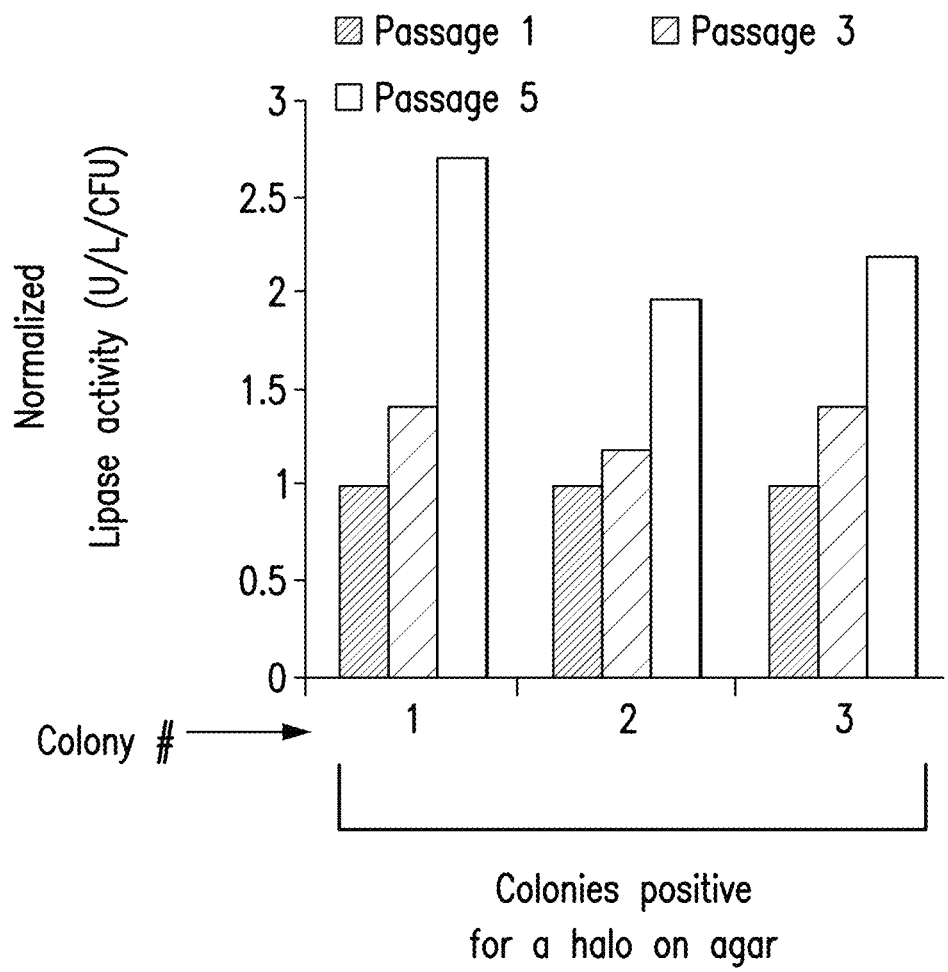

FIG. 5 shows that the lipase activity was increased in probiotics by providing lipid stress.

Figure 6:
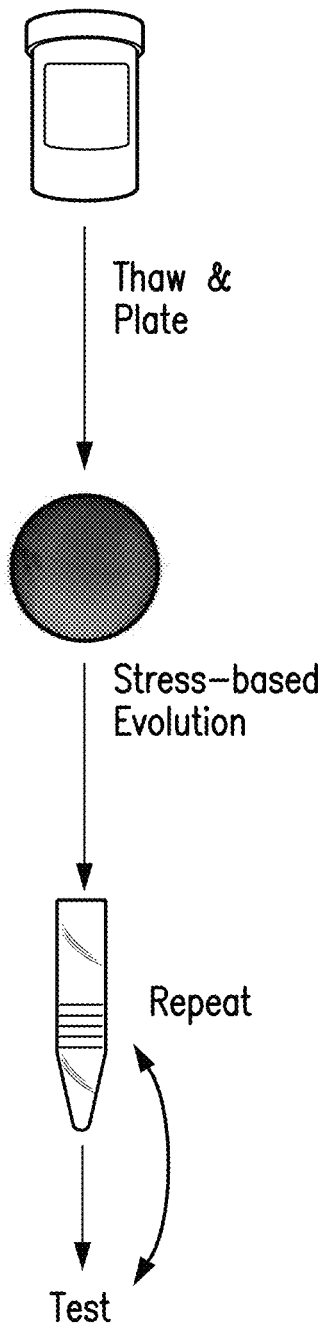

FIG. 6 shows a study design for the isolation and stress-based directed evolution of probiotics in saliva.

Figure 7A:
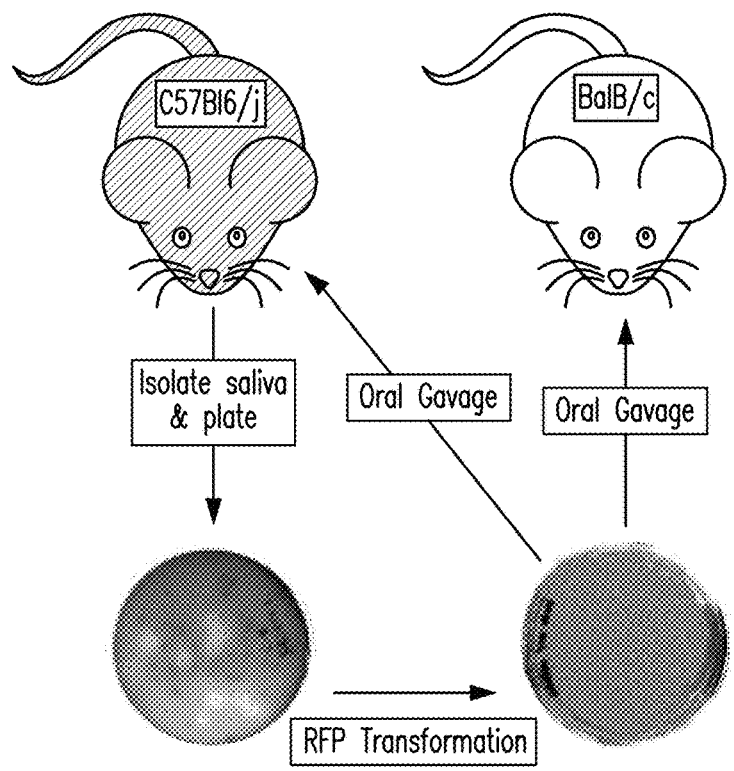
Figure 7B:
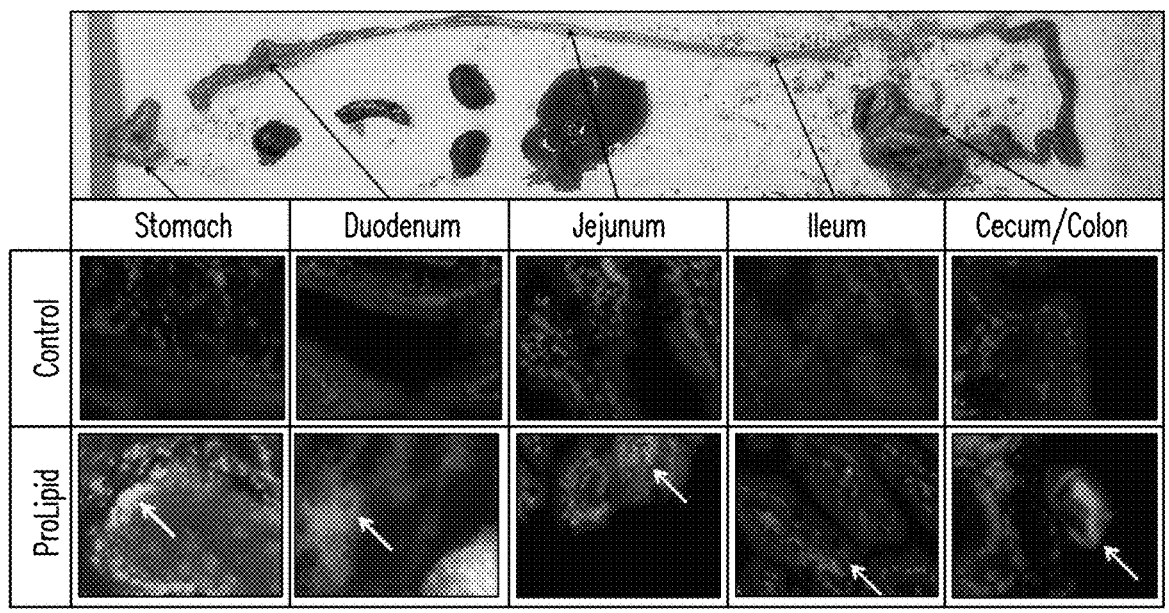

FIGS. 7A-7B show that probiotics of the disclosed subject matter can colonize the GI tract of littermates from which they were isolated at higher levels than a different strain of mice. FIG. 7A shows probiotics of the disclosed subject matter isolated from C57BL/6J mice (B6) were transformed with RFP plasmid and orally gavaged in B6 littermates of isolates and in BALB/c mice. FIG. 7B shows that histology demonstrates that the probiotics of the disclosed subject matter B6 mice colonized in higher numbers in duodenum, jejunum, and cecum in B6 mice as compared to BALB/c mice.

Figures 8A, 8B:
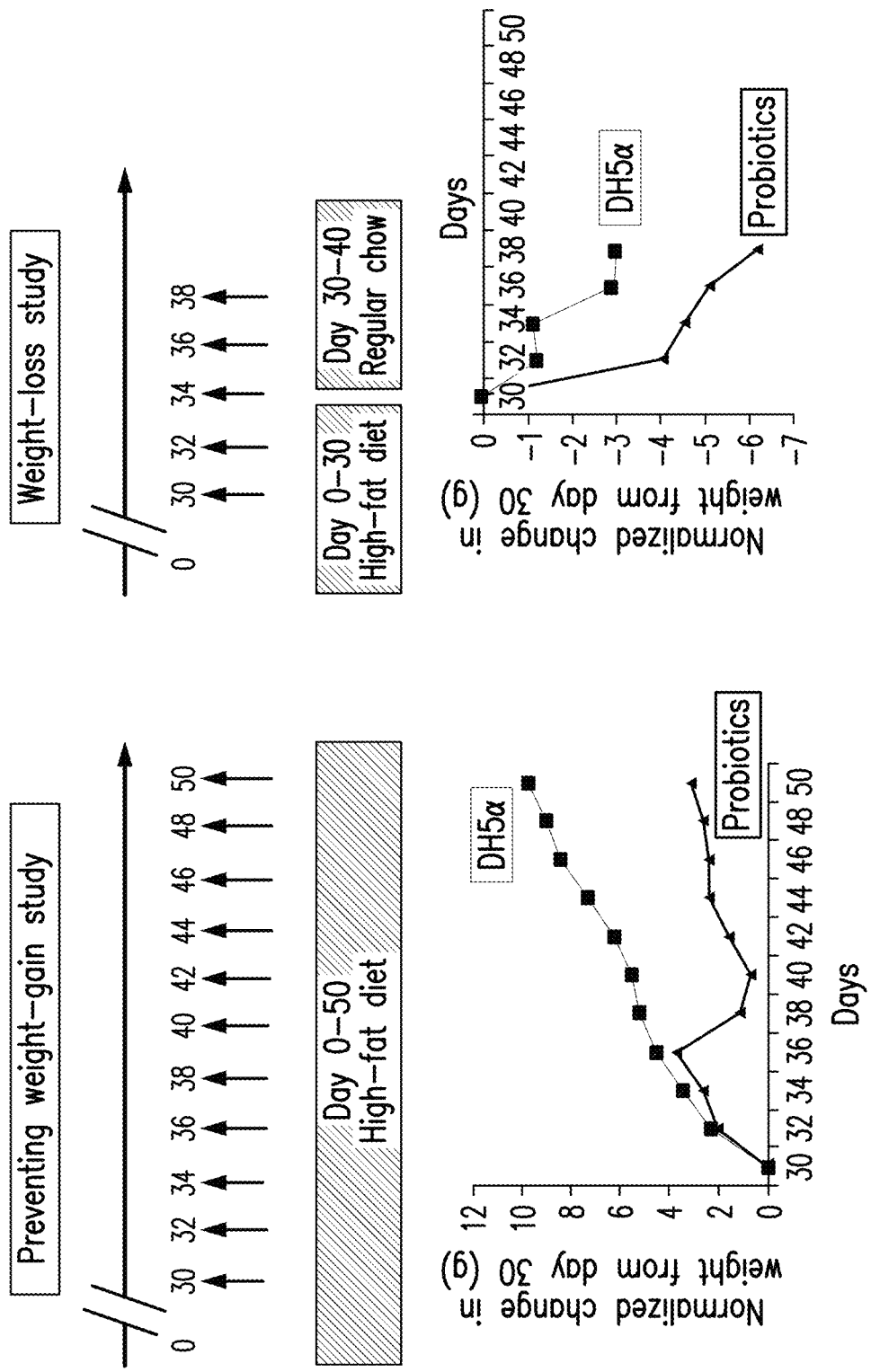

FIGS. 8A-8B show that oral gavage of probiotics of the disclosed subject matter in the presence of high-fat diet prevents weight gain and in conjunction with diet-change leads to weight loss in mice. FIG. 8A shows mice that were orally gavaged with probiotics of the disclosed subject matter gain lower weight overall as compared to DH5α gavaged mice. FIG. 8B shows mice that were orally gavaged with probiotics of the disclosed subject matter lose weight faster in the presence of diet change as compared to DH5α+ regular chow condition.

Figure 9:
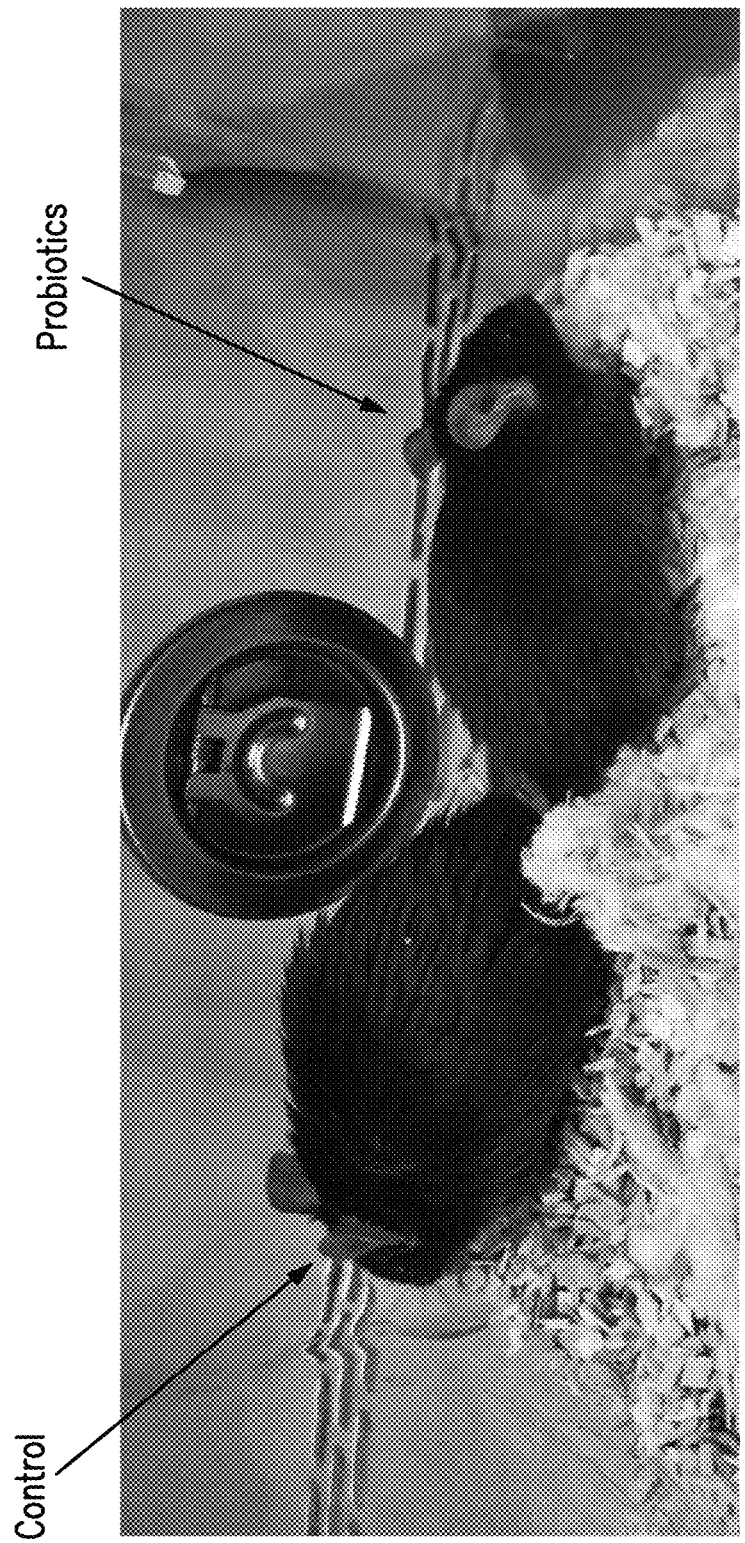

FIG. 9 shows the representative image of mice that were given either DH5α control bacteria or probiotics along with high fat diet, at the end of the study. It was observed that the control group's coat was shinier, and the total body size was bigger than the modified probiotics groups, suggesting lower accumulation of lipids.

Figure 10A:
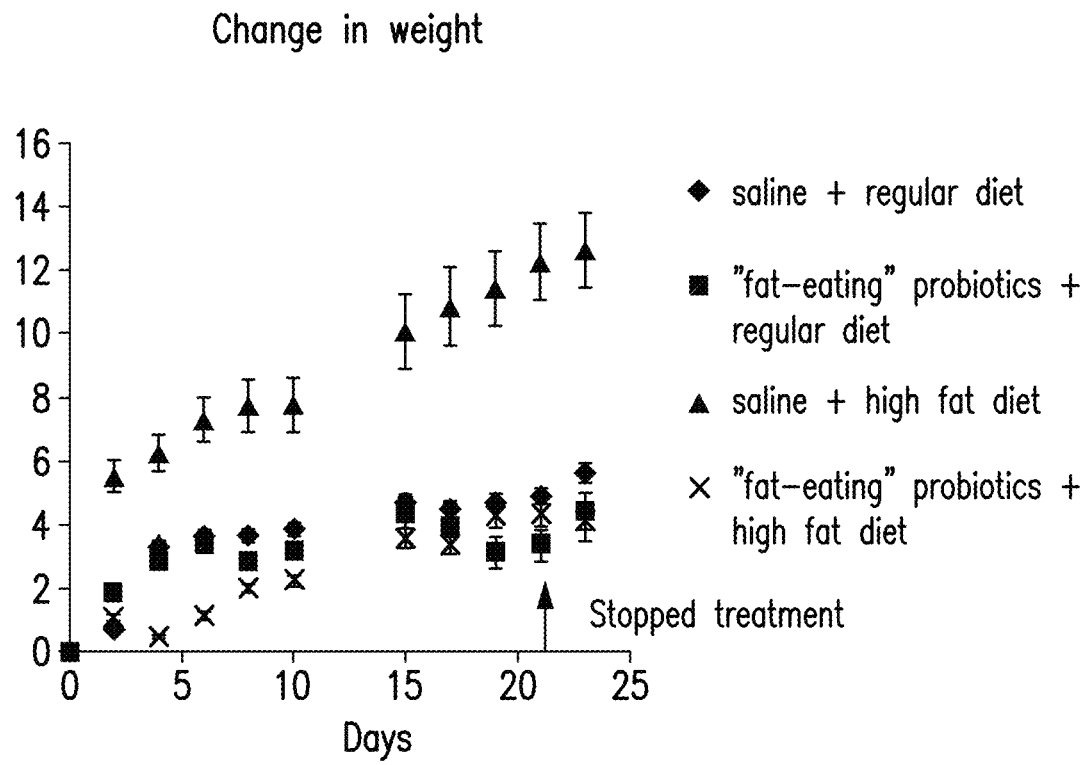
Figure 10B:
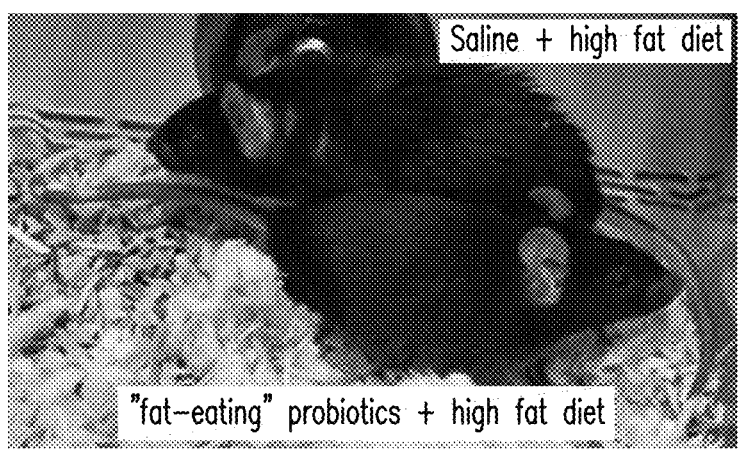

FIGS. 10A-10B show the mice that are on high-fat diet and are given modified lipid metabolism probiotics gain substantially lower amount of weight as compared to the mice that are given high-fat diet and saline. FIG. 10A shows the change of weight over the period of the experiment. FIG. 10B is a representative image of mice that are provided with high-fat diet and treated with saline and provided with high-fat diet and treated with the probiotics.

FIGS. 11A-11E show that the presently disclosed probiotics did not significantly change the metabolism or overall health of the mice in the first 2 days. FIG. 11A shows the study design. FIG. 11B shows the energy expenditure (EE) data normalized to lean mass was not significantly different in the first 2 days between the mice receiving the same type of chow (HFD or RD) (Average±std error). FIG. 11C shows the total movement of mice was significantly higher for Probiotics±HFD group for the first 24 hours, after which this significance was not observed (Average±std error). FIG. 11D shows the food uptake was not significantly different between the mice getting the same type of chow (Average±std error). FIG. 11E shows the final weight (post-96 hours after treatment) of mice getting control bacteria±HFD was significantly higher than all other conditions (Average±stdev), (n=4 per group).

Figure 12:
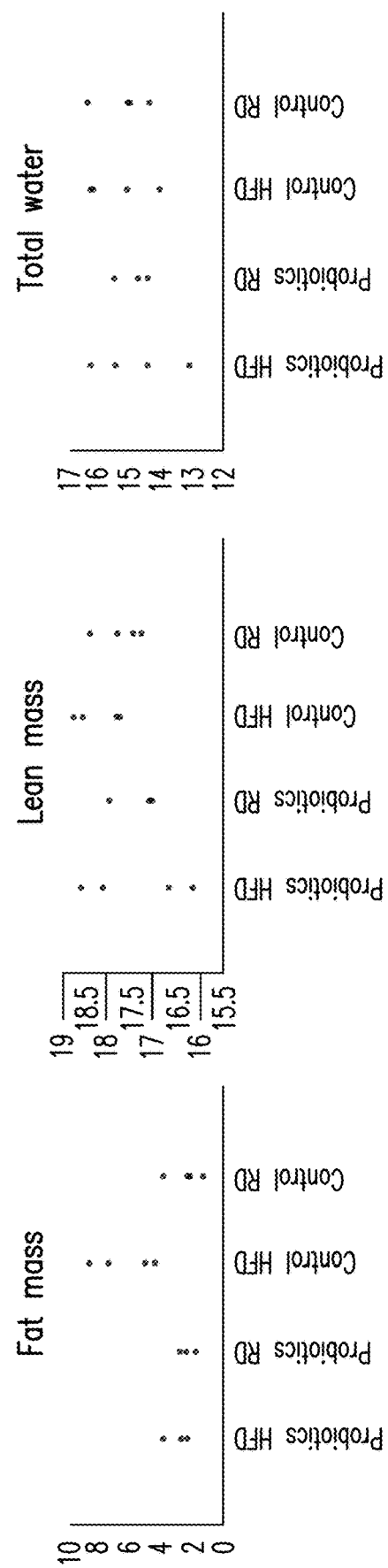

FIG. 12 shows that the presently disclosed probiotics prevented weight gain in mice by reducing the build-up of fat mass in the body.

Figure 13B:
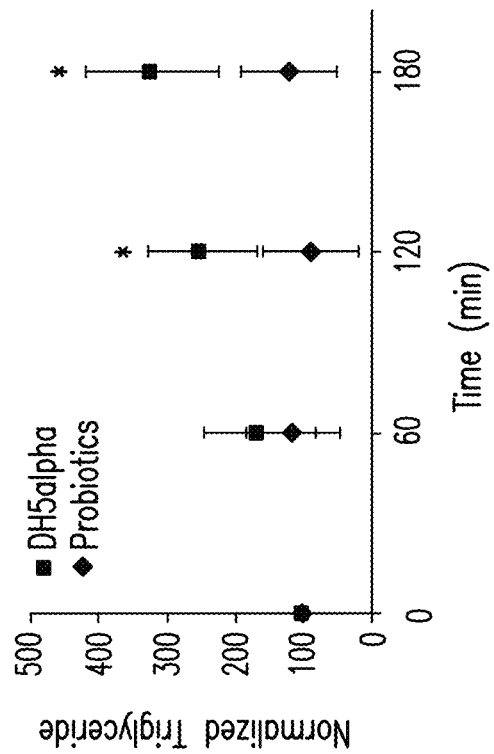
Figure 13A:
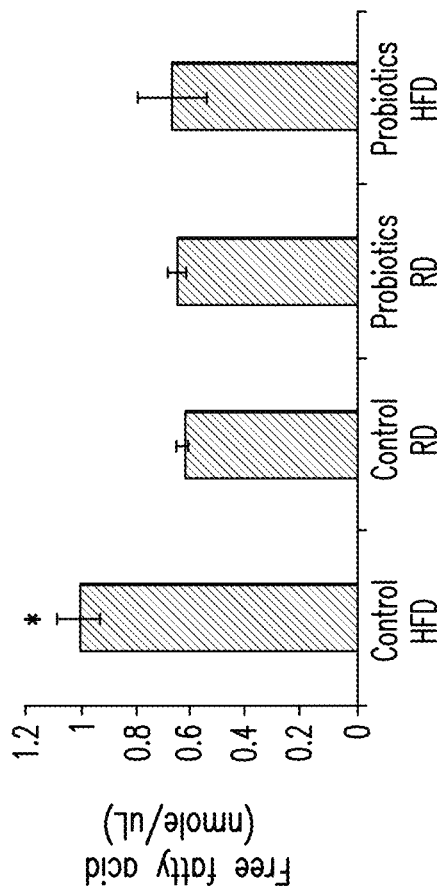

FIGS. 13A-13B show that the presently disclosed probiotics directly prevented build-up of fatty acids and triglycerides in the blood. FIG. 13A shows free fatty acid levels were significantly decreased in Probiotics+HFD group as compared to control bacteria+HFD group, even post-96 hours of treatment. FIG. 13B shows probiotics prevented the up-regulation of triglyceride levels in serum for 3 hours in mice and kept these levels significantly lower than the control bacteria.

FIGS. 14A-14C show that the presently disclosed probiotics induced higher excretion of fat in the stool samples of mice. FIG. 14A shows the study design. FIG. 14B shows probiotics induced significantly higher level of fat excretion in mice as compared to control bacteria. FIG. 14C shows probiotics induced the excretion of Oleic acid significantly higher in mice as compared to control bacteria.

Figure 15:
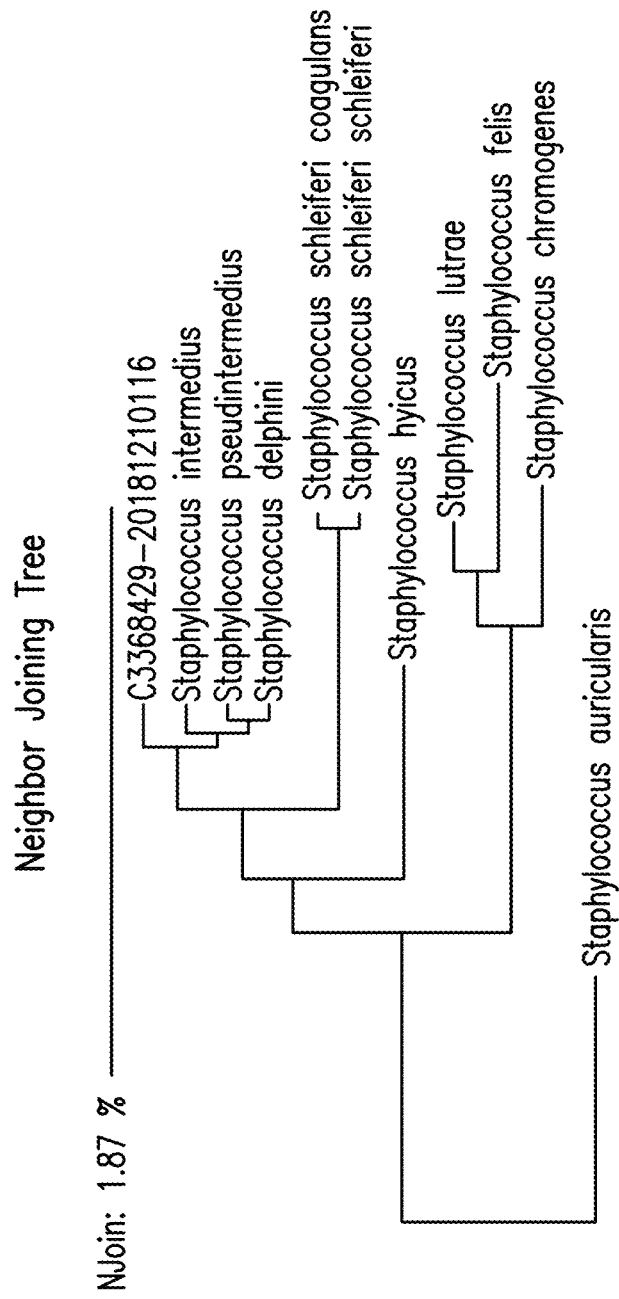

FIG. 15 shows that *Streptococcus intermedius* family of bacteria were found to be the most common bacteria with lipase activity in dog saliva.

Figure 16:
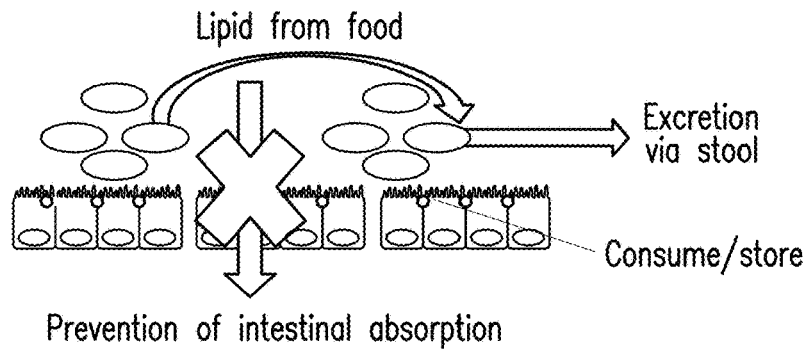

FIG. 16 shows the proposed mechanism of action.

Figure 17:
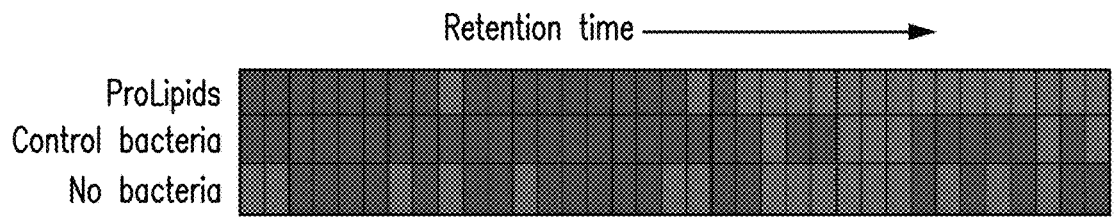

FIG. 17 shows that the presently disclosed probiotics or nonevolved bacteria cultured in lipid-rich media differentially incorporated lipids intracellularly (dark shade-no lipids: light shade-presence of lipids).

Figure 18:
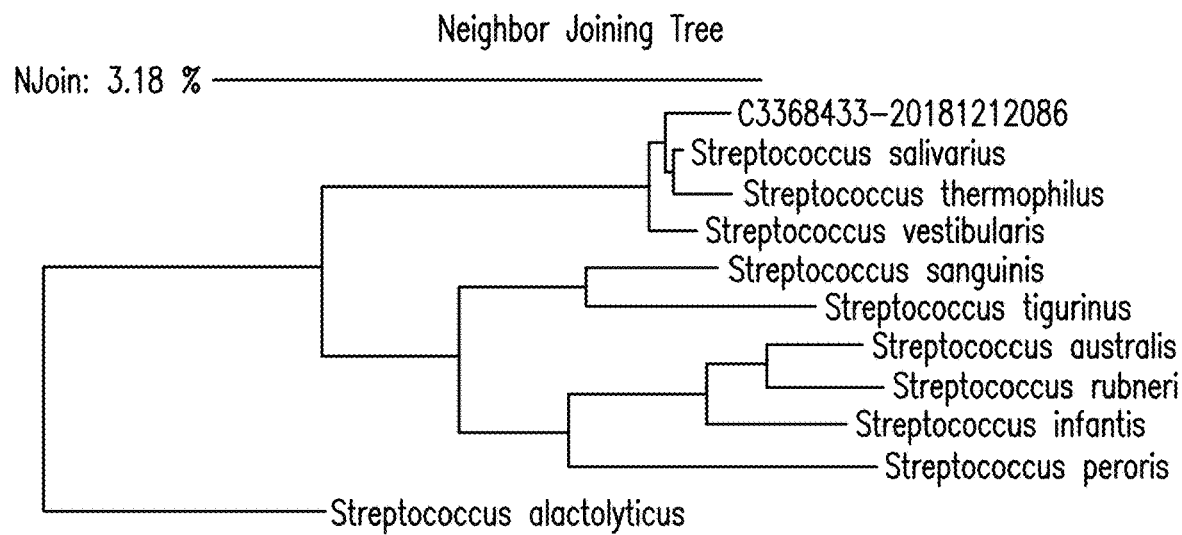

FIG. 18 shows that a benign bacterium *Streptococcus salivarius* was found to be the most common bacteria with lipase activity in human saliva.

5. DETAILED DESCRIPTION OF THE INVENTION

Figure 1:
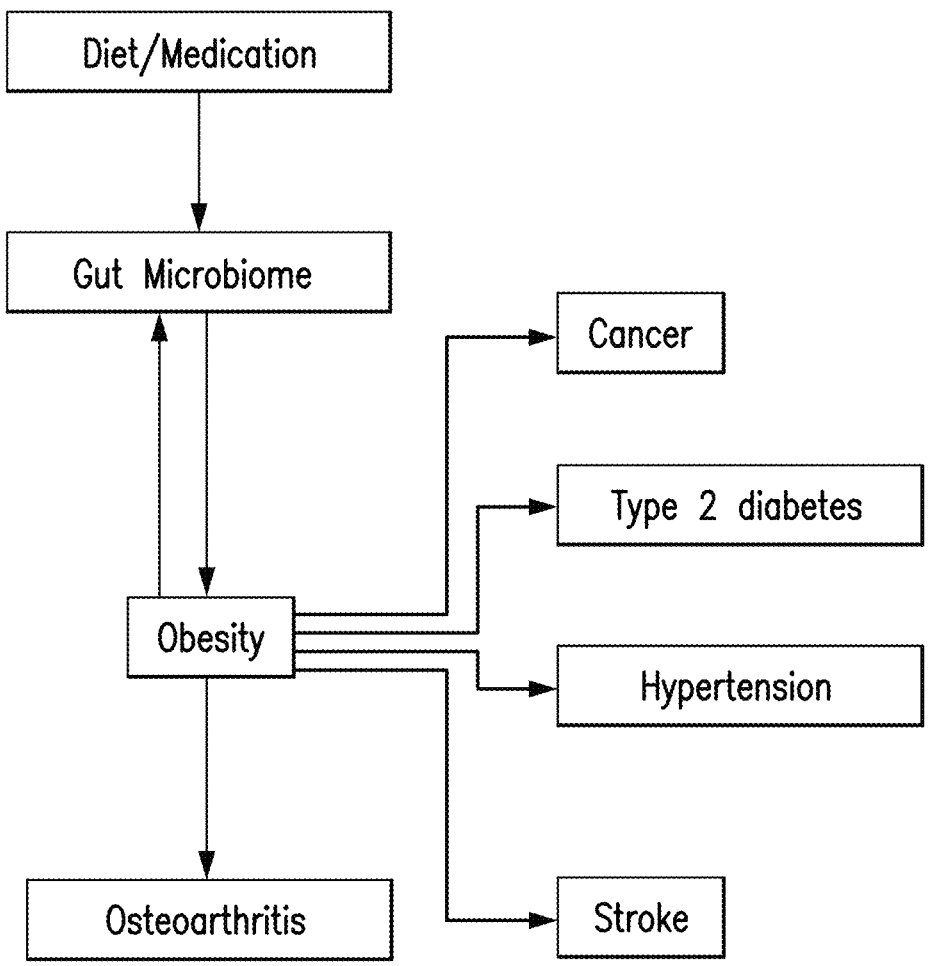
FIG. 1 shows that obesity has been linked to different disorders, such as type 2 diabetes, cardiovascular diseases, hypertension, stroke and certain forms of cancer and shows that the gut microbiota can be a preventive target of obesity.
Figure 2:
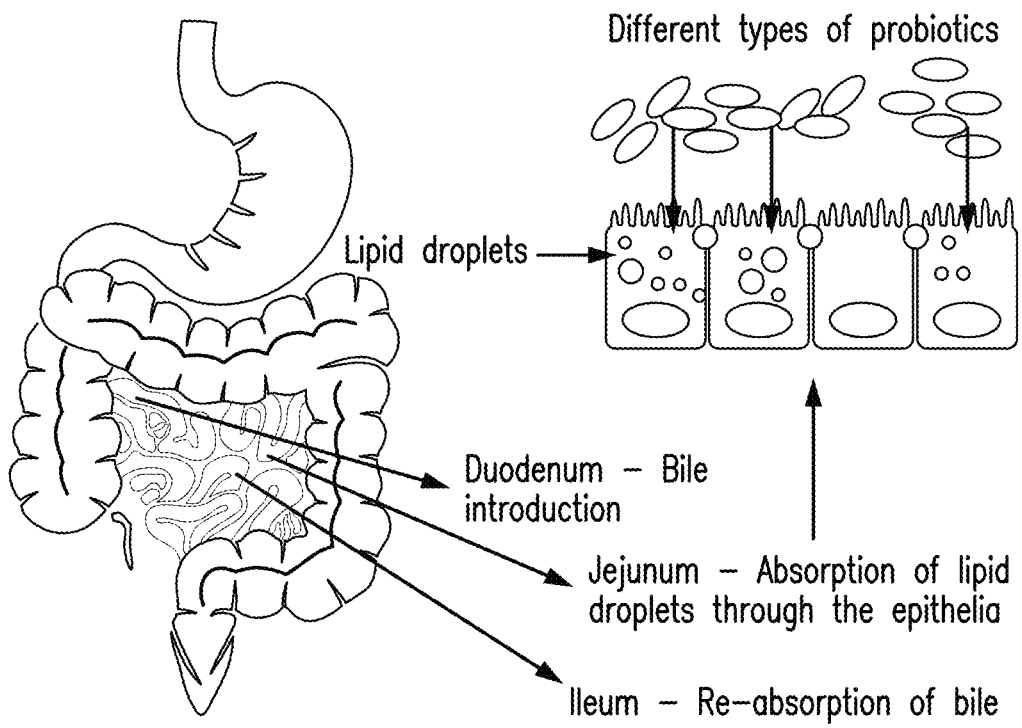
FIG. 2 shows that the microbiota actively modulates the nutrients absorbed in the body and can lead to excess fat deposition through absorption of lipid droplets through the epithelial layer.
Figure 3:
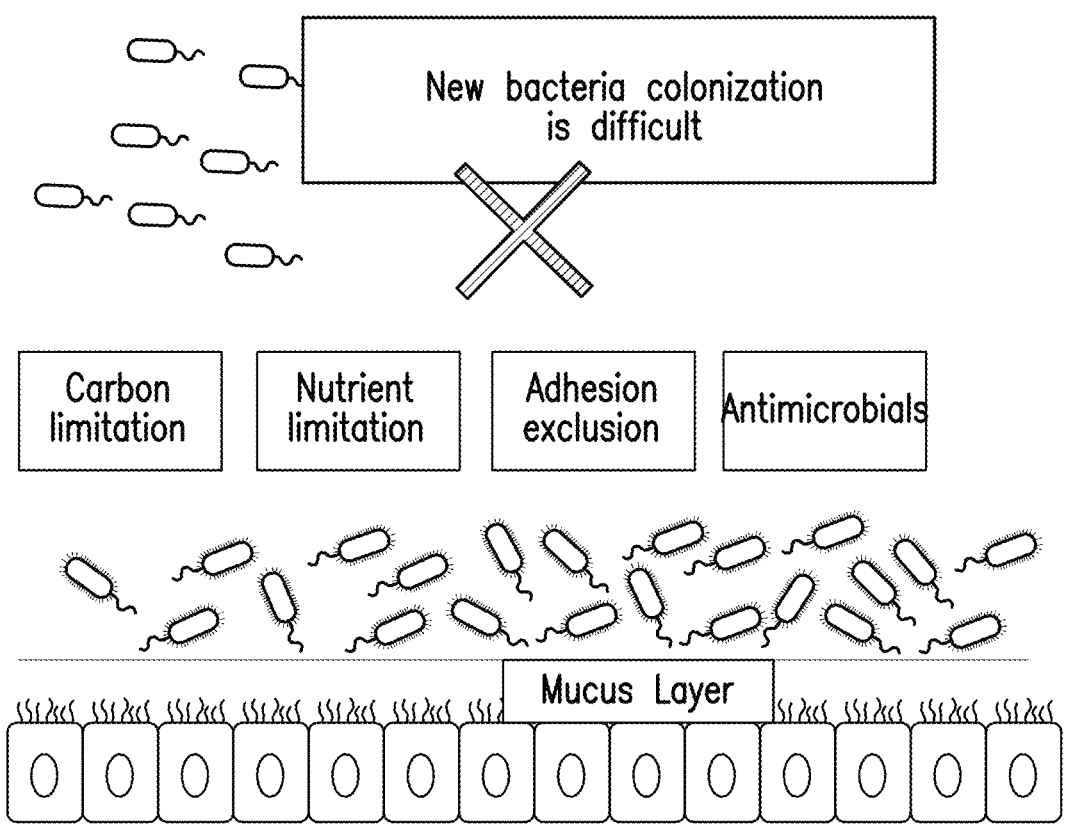
FIG. 3 shows that the microbiota actively prevents colonization of new bacteria.

In recent years, it has been demonstrated that the intestinal microbiota, which are different among individuals,[4] plays an important role in nutrient absorption.[5] Moreover, the microbiota may play a role in intestinal absorption and extra-intestinal metabolism of dietary fat (FIG. 2).[14] Colonization of probiotics in the intestine microbiota is often a difficult task. Existing microbiota, along with the immune system, actively inhibits colonization of new bacteria via prevention of adhesion, carbon source and micronutrient limitation.[15] Colonization by new bacteria may also be inhibited via IgA antibodies of the immune system (FIG. 3).[16]

In one aspect, the present disclosure relates to a probiotics approach modifies the intestinal microbiota composition, and thus modulates the absorption of energy molecules by the host, for example, lipid absorption by the host at the intestines. In another aspect, the present disclosure relates to a novel personalized probiotics approach, by utilizing a host subject's own healthy oral and/or intestinal microbiota, for effective probiotic colonization at the gastrointestinal tract.

For clarity of description, and not by way of limitation, the detailed description of the presently disclosed subject matter is divided into the following subsections:
  5.1 Definitions;
  5.2 Probiotics and Probiotic Compositions;
    5.2.1 Methods of Making;
    5.2.2 Compositions;
  5.3 Methods of Use; and
  5.4 Kits.

5.1 Definitions

The terms used in this specification generally have their ordinary meanings in the art, within the context of the presently disclosed subject matter and in the specific context where each term is used. Certain terms are discussed below, or elsewhere in the specification, to provide additional guidance to the practitioner in describing the compositions and methods of the presently disclosed subject matter and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing," and "comprising" are interchangeable and one of skill in the art is cognizant that these terms are open ended terms.

The term "about" or "approximately" means within an acceptable error range for the particular value as determined by one of ordinary skill in the art, which depends in part on how the value is measured or determined, e.g., the limitations of the measurement system. For example, "about" can mean within 3 or more than 3 standard deviations, per the practice in the art. In certain embodiments, "about" can mean a range of up to 20%, preferably up to 10%, more preferably up to 5%, and more preferably still up to 1% of a given value. In certain embodiments, particularly with respect to biological systems or processes, the term can mean within an order of magnitude, preferably within 5-fold, and more preferably within 2-fold, of a value.

As used herein, the term "bacteria" encompasses both prokaryotic organisms and archaea present in mammalian microbiota. The terms "intestinal microbiota", "gut flora", and "gastrointestinal microbiota" are used interchangeably to refer to bacteria in the digestive tract. The terms "saliva microbiota," "saliva flora," "mouth microbiota," and "mouth flora" are used interchangeably to refer to bacteria found in the oral cavity. As used herein, the term "abundance" refers to the representation of a given phylum, order, family, or genera of microbe present in the digestive tract of a subject.

As used herein, "metabolism" can refer, for example, to lipid metabolism, fatty acid oxidation, or lipogenesis. The terms "modified metabolism" or "change in metabolism" are used interchangeably to refer to a change in the metabolism and/or a change in energy consumption of a probiotic bacterium. The change can be a decrease or an increase in the metabolism or in one or more metabolic pathways of fat and/or lipids of the isolated microbiota of a microbial species, genus, family, strain, order, or class.

As used herein, the term "probiotics" or "probiotic bacteria" refers living bacteria that can be administered to a subject, e.g., orally consumed by a subject. In certain embodiments, the presently disclosed probiotic bacteria or probiotics reduce the absorption of dietary lipids at the gastrointestinal tract of a subject. In certain embodiments, the presently disclosed probiotic bacteria or probiotics have the beneficial effects of modulating (e.g., maintaining or reducing) the body weight of a subject. In certain embodiments, the presently disclosed probiotic bacteria or probiotics have the beneficial effects of treating an overweight or obese subject.

In certain embodiments, the term "microbiota or bacteria having modified metabolism" as used herein, can refer to isolated microbiota or bacteria subject to stress-based directed evolution so that they develop modified metabolism. In certain embodiments, "modified metabolism" can refer to utilization of a specific molecule or category of molecules as a source of energy. In certain embodiments, "modified lipid metabolism" can refer to utilization of lipids as a source of energy. In certain embodiments, sources of energy can comprise lipids and/or fatty acids.

In certain embodiments, the term "microbiota or bacteria having modified metabolism" as used herein, can refer to isolated microbiota or bacteria that exhibit modified metabolism, for example probiotic species having lipid metabolism, as observed by expression of lipase and/or other enzymes involved in lipid metabolism. Probiotics usually do not readily utilize lipid metabolism as energy source and usually have very low, if any, expression of lipases and/or other enzymes involved in lipid metabolism. Therefore, probiotics having increased lipid metabolism can be selected and optionally subject to the directed-based evolution process.

In certain embodiments, probiotics having modified metabolism decrease quantities of energy molecules in the gastrointestinal (GI) tract when administered to a subject, thus decreasing absorption by the subject. In certain embodiments, probiotics having modified metabolism modify the energy molecules, where the modified energy molecules cannot be or are difficult to be absorbed and/or metabolized by the subject. Therefore, change of the metabolism of the probiotics can lead to modification of the content of GI tract and modulation of the amount of energy sources that can be absorbed by the subject.

The term "stress-based directed evolution" of probiotics can refer to an ex-vivo introduction of environmental stressors to the isolated bacteria to enrich the bacteria for the desired trait and encourage the bacteria to enhance their protein production that favors their survival in the presence of stressors. The bacteria are then tested for the desired trait. The steps of screening and stressing can be repeated until the isolated bacteria can survive and proliferate in the presence of stressors. Exemplary stressors can include, for example, presence of lipids and/or fatty acids.

As used herein, a "culture" of bacteria can refer to an in vitro culture of at least one bacterium species. Such bacteria can be cultured with one or more activators or repressors. As used herein, the terms "activators" and "repressors" refer to agents that increase or decrease the number and/or activity and/or metabolism of one or more desired bacteria, respectively.

As used herein, the term "probiotic composition" can refer to a composition containing at least one species, genus, family, strain, order, or class of probiotic bacteria (e.g., a single isolate or a combination of desired bacteria), and can also include any additional carriers, excipients, and/or therapeutic agents that can be administered to a mammal. In certain embodiments, the probiotic composition comprises a buffering agent to allow the probiotic bacteria to survive in the acidic environment of the stomach, that is, the probiotic bacteria resist low pH and are able to survive passage through the stomach to colonize and grow in the intestinal milieu. Buffering agents can include, for example, sodium bicarbonate, milk, yoghurt, infant formula, and other dairy products. In certain embodiments, the probiotic composition is formulated as a food additive. In certain embodiments, the probiotic composition includes other materials known in the art for inclusion in food additives, such as water or other aqueous solutions, starch, binders, thickeners, colorants, flavorants, odorants, acidulants (e.g., lactic acid or malic acid, among others), vitamins, or minerals, among others.

The term "carrier" can refer to a diluent, adjuvant, excipient, or vehicle with which probiotic bacteria can be administered. Such carriers can be, for example, sterile liquids, such as water and oils, including those of petroleum, animal, vegetable or synthetic origin, such as peanut oil, soybean oil, mineral oil, sesame oil and the like. Water or aqueous solution, saline solutions and aqueous dextrose and glycerol solutions can be employed as carriers, particularly for injectable solutions. In certain embodiments, the carrier can be a solid dosage form carrier, including but not limited to one or more of a binder (for compressed pills), a glidant, an encapsulating agent, a flavorant, and a colorant. Suitable carriers are described, for example, in "Remington's Pharmaceutical Sciences" by E. W. Martin.

"Patient" or "subject" or "individual" as used interchangeably herein, refers to a human or non-human subject. Non-limiting examples of non-human subjects include non-human mammals, primates, dogs, cats, mice, rats, guinea pigs, rabbits, pigs, fowl, horses, cows, goats, sheep, cetaceans, etc.

"Treatment" (and grammatical variations thereof such as "treat" or "treating") of a medical condition can include one or more of:
(a) preventing or delaying the appearance of at least one clinical or sub-clinical symptom of the medical condition developing in a subject that can be afflicted with or predisposed to the medical condition, but does not yet experience or display clinical or subclinical symptoms of the medical condition:
(b) clinically intervening in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishing any direct or indirect pathological consequences of the disease, decreasing the rate of disease progression, amelioration or palliation of the disease state and remission or improved prognosis; and
(c) inhibiting the medical condition, e.g., arresting, reducing or delaying the development of the disease or a relapse thereof (in case of maintenance treatment) or at least one clinical or sub-clinical symptom thereof; and/or relieving the medical condition, e.g., causing regression of the state, disorder or condition or at least one of its clinical or sub-clinical symptoms.

The terms "inhibiting," "reducing" or "prevention," or any variation of these terms, referred to herein, includes any measurable decrease or complete inhibition to achieve a desired result. The benefit to a subject to be treated is either statistically significant or at least perceptible to the patient or to the physician. Treatment includes partial or full resolution of symptoms associated with the medical condition to be treated.

"Medical condition" can refer to any weight-related condition, including obesity (Body Mass Index, BMI of about 30 or higher), overweight (BMI of about 25 to about 30), and associated medical conditions and/or conditions where obesity can be a factor including hyperlipidemia, cancer, type 2 diabetes, hypertension, stroke, osteoarthritis, coronary heart disease, sleep apnea and respiratory problems, depression, gallbladder disease. A BMI of about 18.5 to about 25 is considered healthy. In certain embodiments, treatment of a subject and/or a healthy subject comprises maintaining a weight of the subject and/or the healthy subject and/or maintaining a BMI of about 18.5 to about 25 for the subject and/or the healthy subject. In certain embodiments, an obese subject has a BMI of about 30 or higher, an overweight subject has a BMI of about 25 to about 30, a healthy and/or normal subject has a BMI of about 18.5 to about 25.

A "therapeutically effective amount" or "effective amount" as used herein can refer to an amount of a bacterial composition (probiotic) that, when administered to a subject for treating a medical condition, is sufficient to affect such treatment. The "therapeutically effective amount" can vary depending on the composition administered as well as the stage of the medical condition and its severity and the age, weight, physical condition and responsiveness of the subject to be treated. The phrase "acceptable" can refer to compositions that are generally regarded as physiologically tolerable to a patient.

A "microbiome" as used herein can refer to the totality of microbes and their genetic elements (genomes) from a defined environment. A defined environment can, for example, be the intestine and/or the oral cavity of a human being. Thus, microbiome can include all area-specific microbiota and their complete genetic elements.

5.2 Probiotics and Probiotic Compositions

The presently disclosed subject matter relates to probiotics having a modified metabolism and probiotic compositions comprising thereof. The present disclosure also relates to methods of making and modifying the presently disclosed probiotics. In certain embodiments, the probiotics actively modulate processing of energy sources and, therefore, absorption at intestines.

In certain embodiments, the probiotics comprise personalized probiotic bacteria, probiotic bacteria having modified metabolism, or bacteria having a modified metabolism that actively consume energy sources in the gastrointestinal tract of a subject and can decrease the levels of energy sources that are available for absorption in the gastrointestinal tract of a subject. In certain embodiments, the modified metabolism is lipid or fat metabolism. In certain embodiments, the modified metabolism is a modified lipid or fat metabolism. In certain embodiments, the modified lipid metabolism is an increased lipid or fat metabolism.

In certain embodiments, the probiotics and probiotic compositions disclosed herein can be administered to a subject in combination with a diet change from a high-fat in diet to a low-fat diet.

5.2.1 Methods of Making

In certain embodiments, the present disclosure provides a method of making probiotics or a probiotic composition comprising thereof for maintaining body weight in a subject or treating an overweight subject comprising obtaining a microbiota sample from the subject and isolating bacteria from the microbiota sample.

Samples can be obtained and preserved using conventional techniques known in the art. Samples to be tested using the methods described herein can include, but are not limited to, saliva, tooth swab, tooth scrapping, cheek swabs, throat swab, sputum, endogastric sample, feces, and tissue biopsies. In certain embodiments, the microbiota sample is a saliva sample. In certain embodiments, the microbiota sample is a stool sample. In certain embodiments, bacteria are isolated from the multiple species of microbial flora (e.g. Fungi).

Techniques for the isolation and cultivation of microorganisms (e.g., bacteria) include those, for example, described in the Manual of Clinical Microbiology, 8th edition: American Society of Microbiology, Washington D.C., 2003. Bacterial co-cultures can be cultured according to standard practices. In certain embodiments, techniques for the isolation of the microorganisms can be performed via centrifugation. In certain embodiments, a microbiota sample can comprise one or more bacteria species selected from Table 1.

In certain embodiments, a microbiota sample can comprise bacteria of one or more of phyla Actinobacteria, Bacteroidetes, Chlamydiae, Chloroflexi, Eury archaeota, Firmicutes, Fusobacteria, Proteobacteria, Spirochaetes, SR1, Synergistetes, Tenericutes, and TM7. In certain embodiments, a microbiota sample can comprise bacteria of one or more of *Rothia* genus, *Escherichia* genus, and specific species, for example and not by way of limitation, *R. nasimurium*.

In certain embodiments, a microbiota sample can comprise bacteria obtained from commercial sources, for example, ATCC.

In certain embodiments, individual species of the bacteria is isolated using lipolytic agar plates. In certain embodiments, bacteria isolated from the saliva are identified using MALDI-TOF or comparative sequencing of the 16S ribosomal RNA (rRNA) gene in bacteria. In certain embodiments, the isolated bacteria can be subject to stress-based directed evolution to develop probiotic bacteria having modified metabolism as compared to isolated bacteria that are not subject to stress-based directed evolution. Stress-directed evolution comprises introducing environmental stressors to the bacteria culture to enrich the bacteria for the desired trait and encourage the bacteria to enhance their protein production that favors their survival in the presence of stressors.

In certain embodiments, the bacteria thus isolated can be cultured in a 5 to 100 mL broth of energy source. In certain embodiments, energy source can be in the form of lipids, for example but not by way of limitation, soybean oil, Tween 20, Tween®80 or any other lipid molecule. In certain embodiments, the lipid concentration can range from 1% to 100% v/v in the broth. In certain embodiments, the broth is made using by adding lipids to sterile saline solution at 1% to 20% vol/vol.

TABLE 1

Exemplary bacteria commonly found on the surfaces of the human body.

| BACTERIUM | Skin | Conjunctiva | Nose | Pharynx | Mouth | Lower GI | Ant. urethra | Vagina |
|---|---|---|---|---|---|---|---|---|
| *Staphylococcus epidermidis* | ++ | + | ++ | ++ | ++ | + | ++ | ++ |
| *Staphylococcus aureus** | + | +/– | + | + | + | ++ | +/– | + |
| *Streptococcus mitis* | | | | + | ++ | +/– | + | + |
| *Streptococcus salivarius* | | | | ++ | ++ | | | |
| *Streptococcus mutans** | | | | + | ++ | | | |
| *Enterococcus faecalis** | | | | +/– | + | ++ | + | + |
| *Streptococcus pneumoniae** | | +/– | +/– | + | + | | | +/– |
| *Streptococcus pyogenes** | +/– | +/– | | + | + | +/– | | +/– |
| *Neisseria* sp. | | + | + | ++ | + | | + | + |
| *Neisseria meningitidis** | | | + | ++ | + | | | + |
| Enterobacteriaceae* (*Escherichia coli*) | | +/– | +/– | +/– | + | ++ | + | + |
| *Proteus* sp. | | +/– | + | + | + | + | + | + |
| *Pseudomonas aeruginosa** | | | | +/– | +/– | + | +/– | |
| *Haemophilus influenzae** | | +/– | + | + | + | | | |
| *Bacteroides* sp.* | | | | | | ++ | + | +/– |
| *Bifidobacterium bifidum* | | | | | | ++ | | |
| *Lactobacillus* sp. | | | | + | ++ | ++ | | ++ |
| *Clostridium* sp.* | | | | | +/– | ++ | | |
| *Clostridium tetani* | | | | | | +/– | | |
| Corynebacteria | + | + | ++ | + | + | + | + | + |
| Mycobacteria | + | | +/– | +/– | | | + | + |
| Actinomycetes | | | | + | + | | | |
| Spirochetes | | | | + | ++ | ++ | | |
| Mycoplasmas | | | | + | + | + | +/– | + |

Potential pathogens are denoted by an asterisk; "++" indicates that the bacterium represents nearly 100% of the population; "+" indicates that the bacterium represents ~25% of the population; and "+/–" indicates that the bacterium represents less than 5% of the population. Kenneth Todar, Ph.D., Online Textbook of Bacteriology, © 2011; www.textbookofbacteriology.net/normal-flora.html.

In certain embodiments, the isolated bacteria can be subject to stress-based directed evolution to develop probiotic bacteria having modified metabolism, compared to isolated bacteria that are not subject to stress-based directed evolution. In certain embodiments, the modified metabolism comprises modified lipid metabolism.

In certain embodiments, the modified lipid metabolism comprises increased lipase expression. In certain embodiments, the modified lipid metabolism comprises increased expression of enzymes involved in lipid metabolism.

In certain embodiments, the lipid metabolism refers to fatty acid oxidation mediated energy generation and/or lipogenesis (generation of fat). In certain embodiments, the isolated bacteria are grown on cholesterol as the sole carbon source in order to select probiotic bacteria that are capable of lowering cholesterol when administered to a subject.

In certain embodiments, the probiotic bacteria having modified lipid metabolism are developed by culturing the isolated bacteria in increasing levels of lipids. In certain embodiments, the isolated bacteria are cultured in a culture media having at least about 1% v/v lipids (1% lipids in 99% culture medium), then in a culture media having at least about 2% v/v lipids then in a culture media having at least about 5% lipids, then in a culture media having at least about 10% lipids, then in a culture media having at least about 20% lipids, then in a culture media having at least about 40% lipids, and then in a culture media having at least about 100% v/v lipids.

In certain embodiments, the percentage of lipid content in the culture is increased by at least about 5% v/v. In certain embodiments, the percentage of lipid content in the culture is increased by at least about 0.01% increment from 0% to 100% v/v lipid in the culture medium. For example, and not by way of limitation, isolated bacteria are cultured in the presence of at least about 0.01%, of at least about 0.05%, of at least about 0.1%, of at least about 0.2%, of at least about 0.4%, of at least about 0.6%, of at least about 0.8%, at least about 1%, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, and/or at least about 100% v/v lipids in the culture medium.

In certain embodiments, the survival and proliferation of the isolated bacteria in the increasing levels of lipids is evaluated.

In certain embodiments, metabolic activities of the probiotic bacteria that are subjected to stress-based directed evolution are evaluated. Probiotic bacteria having modified lipid metabolism can be isolated. In certain embodiments, the probiotic bacteria having modified lipid metabolism utilize lipids as a source of energy. In certain embodiments, the probiotic bacteria having modified lipid metabolism can prevent lipid absorption by the subject by actively decreasing the amount of lipids available for absorption in the gastrointestinal tract of the subject.

In certain embodiments, the probiotic bacteria having modified lipid metabolism can exhibit modified lipolytic activity, modified fatty acid metabolism, and/or modified lipase activity. In certain embodiment the probiotic bacteria having modified lipid metabolism can survive in culture medium containing at least about 50%, at least about 60%, at least about 70%, at least about 80%, at least about 90%, at least about 95%, at least about 99%, or at least about 100% v/v lipids.

In certain embodiments, the probiotic bacteria subject to stress-based directed evolution can exhibit an increased metabolism that is at least about 1%, at least about 10%, at least about 15%, at least about 20%, at least about 30%, at least about 50%, or at least about 100% increase as compared to isolated bacteria that are not subject to stress-based directed evolution.

In certain embodiments, probiotic bacteria having modified lipase activity are selected from a group of bacteria isolated from a saliva microbiota sample. Next, these probiotic bacteria can be cultured in an environment of modified or increasing lipid concentrations to further increase their dependency on lipids for energy.

In certain embodiments, lipase activity is measured in the isolated bacteria. In certain embodiments, the lipase activity is required for having lipids as an energy source. Non-limiting examples of lipids include triglycerides, glycerol, phospholipases, Tween®80, Tween®20, soy bean oil, vegetable oil, olive oil, peanut oil, butyric acid, lauric acid, myristic acid, palmitic acid, stearic acid, Propionic acid-Propanoic acid, Butyric acid-Butanoic acid, Valeric acid-Pentanoic acid, Caproic acid-Hexanoic acid, Enanthic acid-Heptanoic acid, Caprylic acid-Octanoic acid, Pelargonic acid-Nonanoic acid, Capric acid-Decanoic acid, Undecylic acid-Undecanoic acid, Lauric acid-Dodecanoic acid, Tridecylic acid-Tridecanoic acid, Myristic acid-Tetradecanoic acid, Pentadecylic acid-Pentadecanoic acid, Palmitic acid-Hexadecanoic acid, Margaric acid-Heptadecanoic acid, Stearic acid-Octadecanoic acid, Nonadecylic acid-Nonadecanoic acid-Arachidic acid-Eicosanoic acid, Heneicosylic acid-Heneicosanoic acid, Behenic acid-Docosanoic acid, Tricosylic acid-Tricosanoic acid, Lignoceric acid-Tetracosanoic acid, Pentacosylic acid-Pentacosanoic acid, Cerotic acid-Hexacosanoic acid, Heptacosylic acid-Heptacosanoic acid, Montanic acid-Octacosanoic acid, Nonacosylic acid-Nonacosanoic acid, Melissic acid-Triacontanoic acid, Henatriacontylic acid-Henatriacontanoic acid, Lacceroic acid-Dotriacontanoic acid, Psyllic acid-Tritriacontanoic acid, Geddic acid-Tetratriacontanoic acid, Ceroplastic acid-Pentatriacontanoic acid, and Hexatriacontylic acid-Hexatriacontanoic acid.

In certain embodiments, the steps of screening and stressing can be repeated until the probiotic bacteria derived from the bacteria isolated from the microbiota sample can survive and proliferate in a modified lipid environment. In certain embodiments, the "modified lipid environment" refers to an environment that includes an increased lipid level or a modified composition of different lipids (e.g., saturated fats, unsaturated fats) as compared to an environment where the bacteria are isolated from. In certain embodiments, the "modified lipid environment" refers to an environment that includes dye labeled or unlabeled lipids, 13C labeled or unlabeled lipids, deuterated or un-deuterated lipids, lipids that cannot be metabolized, and/or lipids that form complex structures (e.g., lipidoids, liposomes, micelles etc.)

In certain embodiments, the isolated bacteria are tested for their lipolytic activity and bacteria having modified lipolytic activity are selected. The selected bacteria are either used in a probiotic composition or are first subject to a stress-based directed evolution and then used in the probiotic composition.

In certain embodiments, the isolated bacteria are grown in conditions similar to a modified fat diet, for example, a western-style diet. Probiotic bacteria selected from the cultures are conditioned to flourish in an unhealthy environment, where the unhealthy environment comprises a modified lipid content. In certain embodiments, the probiotic bacteria provide a therapeutic benefit following administration to an overweight subject.

As used herein, the term "healthy diet" refers to a diet that can reduce the risk of cardiovascular diseases, cancer, diabetes and other conditions linked to obesity. As used herein, the term "healthy environment refers to an environment that comprises similar lipid levels and/or compositions as a healthy diet. As used herein, the term "modified fat diet" refers to a diet comprising an increased lipid level or a modified composition of different lipids (e.g., saturated fats, unsaturated fats) as compared to a healthy diet. As used herein, the term "modified lipid content" refers to an increased lipid level or a modified composition of different lipids (e.g., saturated fats, unsaturated fats) as compared to the lipid level or lipid composition in a healthy environment.

In certain embodiments, the probiotic bacteria having modified metabolism can be conditioned such that the probiotic bacteria are optimized for administration to a particular environment, for example, the intestine, a mucosal surface, etc.). That is, in the manufacturing process of a probiotic culture, a combination, of microbes is cultured such that they flourish in the gastrointestinal tract of a subject. In certain embodiments, probiotic bacteria having modified metabolism are also cultured with microbes expected to be in the environment to be treated. Such in vitro conditioning prior to in vivo administration can generate a bacterial culture that is able to survive the milieu of a target site that is contributing to a medical condition.

In certain embodiments, activators and/or repressors can be added to the cultures to enhance or decrease the metabolic activity of one or more species of bacteria. Activators and repressors are known in the art. Genetic manipulation of probiotics for enhanced lipid metabolism or inhibition of enzymes such as phospholipases or lipases using small molecules for repressing metabolism can be used.

In certain embodiments, provided herein is a probiotic composition or culture comprising culture of *Rothia nasimurium* and *Escherichia coli* bacteria to treat obesity.

In certain embodiments, provided herein is a probiotic composition or culture comprising microbes of genera such as, for example, *Rothia* and *Escherichia* for treatment of obesity.

In certain embodiments, provided herein is a culture for conditioning as described above for treatment of obesity which can comprise one or more of the following bacteria: *Rothia nasimurium* and *Escherichia coli*.

In certain embodiments, the probiotic bacteria having modified metabolism are included in the probiotic composition. In certain embodiments, a probiotic composition can comprise one or more of the bacteria species included in Table 1.

In certain embodiments, a genetic analysis of the isolated bacteria is performed, to identify lineage and the susceptibility of these bacteria to different antibiotics and to determine pathogenicity.

In certain embodiments, the probiotic bacteria are personalized probiotic bacteria, where the probiotic bacteria having modified metabolism are administered to the same subject where the probiotic bacteria are derived from. Therefore, the probiotic bacteria are personalized and have higher capability of colonizing the intestinal mucosa because the probiotic bacteria are derived from bacteria that were part of the gut environment, and thus the immune system recognizes these bacteria as part of the microbiome.

The use of such personalized probiotic bacteria can allow the use of lower therapeutic amounts due to higher protein expression and can simultaneously allow the patient to avoid any potential harmful side-effects associated with reintroduction of specific bacterial strains.

In certain embodiments, the development of personalized probiotic bacteria having modified metabolism, such as bacteria isolated by a subject can allow the use of lower therapeutic amounts due to higher metabolic activity and can further allow the subject to avoid any potential harmful side-effects associated with reintroduction of specific bacterial strains.

5.2.2 Probiotic Compositions

The presently disclosed subject matter further provides probiotic compositions comprising probiotic bacteria having modified metabolism as disclosed herein. Probiotic compositions are formulated relative to an administration route. In certain embodiments, a probiotic composition of the presently disclosed subject matter comprises an effective amount of probiotic bacteria having modified metabolism as disclosed herein, combined with an acceptable carrier. "Acceptable carrier," as used herein, includes any carrier which does not interfere with the effectiveness of the biological activity of the active ingredients and/or that is not toxic to the subject receiving such ingredients. Non-limiting examples of acceptable carriers include phosphate buffered saline solutions, water, emulsions, such as oil/water emulsions, various types of wetting agents and sterile solutions. Additional non-limiting examples of compatible carriers can include any suitable vehicle, delivery or dispensing means or material. Such acceptable carriers can be formulated by conventional methods and can be administered to the subject at an effective amount.

In certain embodiments, the probiotic composition is formulated as a food additive. In certain embodiments, the food additive disclosed herein further comprises other materials known in the art for inclusion in food additives, including, but not limited, water or other aqueous solutions, starch, binders, thickeners, colorants, flavorants, odorants, acidulants (e.g., lactic acid or malic acid, among others), vitamins, minerals, and combinations thereof. In certain embodiments, the food additive comprises between about $10^3$ and about $10^4$ CFU probiotic bacteria per gram of the food additive, between about $10^4$ and about $10^5$ CFU probiotic bacteria per gram of the food additive, between about $10^5$ and about $10^6$ CFU probiotic bacteria per gram of the food additive, between about $10^6$ and about $10^7$ CFU probiotic bacteria per gram of the food additive.

The present disclosure also provides a fortified food comprising the probiotics or probiotic compositions disclosed herein. In certain embodiments, the fortified food disclosed herein further comprises a base food. In certain embodiments, the food additive can be incorporated to a base food to form the fortified food. Any base foods known in the art can be used with the present disclosure. Non-limiting examples of base foods include kefir, yakult, miso, natto, tempeh, kimchee, sauerkraut, water, milk, fruit juices, vegetable juices, yogurt, carbonated soft drinks, non-carbonated soft drinks, coffee, tea, beer, wine, liquor, alcoholic mixed drinks, bread, cakes, cookies, crackers, extruded snacks, soups, frozen desserts, fried foods, pasta products, potato products, rice products, corn products, wheat products, dairy products, confectionaries, hard candies, nutritional bars, breakfast cereals, bread dough, bread dough mix, sauces, processed meats, and cheeses.

Administration of a probiotic composition comprising probiotic bacteria having modified metabolism can be accomplished by any method likely to introduce the bacteria into the desired location. In certain embodiments, the probiotics can be administered to a subject, in the form of a food additive or a fortified food disclosed herein, by oral consumption. In certain embodiments, the probiotic bacteria can be mixed with a carrier and (for easier delivery to the digestive tract) be applied to liquid or solid food, feed, or drinking water. The carrier material should be non-toxic to the bacteria and the subject/patient. In certain embodiments, the carrier contains an ingredient that promotes viability of the bacteria during storage. The formulation can include added ingredients to improve palatability and improve shelf-life. If a reproducible and measured dose is desired, the bacteria can be administered by a rumen cannula.

In certain embodiments, the carrier comprises a diluent, adjuvant, excipient, or vehicle with which probiotic bacteria are administered. In certain embodiments, the carrier can be sterile liquids, such as water and oils, including those of petroleum, animal, vegetable or synthetic origin, such as peanut oil, soybean oil, mineral oil, sesame oil and the like. In certain embodiments, the carrier can be water or aqueous solution, saline solutions and aqueous dextrose and glycerol solutions. In certain embodiments, the carrier can be a solid dosage form carrier, including but not limited to one or more of a binder (for compressed pills), a glidant, an encapsulating agent, a flavorant, and a colorant. Suitable carriers for therapeutic use are well known in the art and are described, for example, in "Remington's Pharmaceutical Sciences" by E. W. Martin, and in "Remington: The Science and Practice of Pharmacy." Lippincott Williams & Wilkins.

The choice of a carrier can be selected based on the intended route of administration and standard practice. In certain embodiments, oral delivery can be used for delivery to the digestive tract. In certain embodiments, oral formulations comprise additional mixtures, such as milk, yogurt, and infant formula.

In certain embodiments, the duration and frequency of administration can vary between overweight and obese subjects or even between different subjects.

In certain embodiments, solid dosages in the form of tablets are used for the delivery of the probiotic bacteria by mixing the probiotic bacteria having modified metabolism with one or more components selected from the group consisting of sodium alginate, calcium carbonate, glyceryl monooleate, triethyl citrate, acetylated monoglyceride, and hypromellose acetate succinate (HPMCAS).

In certain embodiments, the probiotic bacteria or probiotic compositions disclosed herein can be administered parenterally.

In certain embodiments, the probiotic bacteria or probiotic compositions of the presently disclosed subject matter can be prepared for delivery as a solution, a tablet, or as a lyophilized culture. Where cultures are lyophilized, the preparation can be rehydrated in, for example, yogurt or water for administration.

In certain embodiments, the probiotic bacteria or probiotic compositions of the presently disclosed subject matter are formulated such that they can survive passage through the acidic environment of the stomach and such that they adjust quickly to the intestinal environment. Such formulation allows the presently described probiotic bacteria and probiotic compositions to have an elongated half-life in the intestines.

In certain embodiments, the probiotics or probiotic compositions disclosed herein are administered to a subject who has a healthy BMI. In certain embodiments, the probiotics or probiotic compositions disclosed herein are administered to a subject who has an overweight BMI. In certain embodiments, the probiotics or probiotic compositions disclosed herein are administered to a subject who have a diagnosed disease, e.g., obesity. In certain embodiments, the probiotics or probiotic compositions are administered to the subject in the form of food additives or fortified foods disclosed herein. Dosage of the probiotic bacteria or probiotic composition disclosed herein for the subject (e.g., a subject having a healthy BMI, a subject having an overweight BMI, a subject having an obese BMI, a subject diagnosed with obesity) can vary depending upon the characteristics of the subject (e.g., age, sex, race, weight, height, BMI, body fat percentage, and/or medical history), frequency of administration, manner of administration, clearance of the probiotic bacteria from the subject, and the like.

In certain embodiments, the initial dose can be larger, followed by smaller maintenance doses. In certain embodiments, the dose can be administered as infrequently as weekly or biweekly, or fractionated into smaller doses and administered daily, semi-weekly, etc., to maintain an effective dosage level. In certain embodiments, a variety of doses are effective to achieve colonization of the gastrointestinal tract with the desired probiotic bacterial, for example and not by way of limitation, about $10^6$ CFU, about $10^7$ CFU, about $10^8$ CFU, about $10^9$ CFU, about $10^{10}$ CFU, about $10^{11}$ CFU, about $10^{12}$ CFU, about $10^{13}$ CFU, about $10^{14}$ CFU, or about $10^{14}$ CFU of probiotic bacteria can be administered in a single dose to a subject. In certain embodiments, lower doses can also be effective, for example and not by way of limitation, about $10^4$ and about $10^5$ CFU of probiotic bacteria. In certain embodiments, the probiotic bacteria are administered to a subject in a dosage of between about $10^6$ and about $10^7$ CFU, between about $10^7$ and about $10^8$ CFU, between about $10^8$ and about $10^9$ CFU, between about $10^9$ and about $10^{10}$ CFU, between about $10^{10}$ and about $10^{11}$ CFU, between about $10^{11}$ and about $10^{12}$ CFU, between about $10^{12}$ and about $10^{13}$ CFU, between about $10^{13}$ and about $10^{14}$ CFU, or between about $10^{14}$ and about $10^{15}$ CFU. In certain embodiments, the probiotic bacteria are administered to a subject in a dosage of about $10^{10}$ CFU of probiotics. In certain embodiments, the probiotic bacteria are administered to a subject in a dosage of up to about $10^{12}$ CFU. In certain embodiments, the subject is a human. In certain embodiments, the subject is a domestic animal, e.g., a canine.

In certain embodiments, when administered to a subject having a diagnosed disease (e.g., obesity) or a subject having an obese BMI, the optimal dosage can be empirically determined by treating physicians based on the stage of disease and patient statistics (e.g., age, height, weight, etc.). In certain embodiments, when administered to a subject who has a healthy BMI, or an overweight BMI, the optimal dosage can be empirically determined by the subject or a dietitian based on the subject's statistics, e.g., age, sex, race, height, weight, BMI, body fat percentage, and/or medical history.

In certain embodiments, a probiotic composition or probiotic bacteria disclosed herein can be delivered every 4, 12, 24, 36, 48, 60, or 72 hours. In certain embodiments, the probiotic composition or the probiotic bacteria can be delivered with at least one second pharmaceutically active ingredient, where the second pharmaceutically active ingredient can be delivered simultaneously or sequentially (e.g., within a 4, 12, 24-hour or 1-week period) with the probiotic composition or the probiotic bacteria. In certain embodiments, the probiotic composition or the probiotic bacteria can be delivered with two, three, four, five, or six second pharmaceutically active ingredients. In certain embodiments, the treatment can last for at least about 1 week, at least about 2 weeks, at least about 3 weeks, at least about 4 weeks, at least about 5 weeks, at least about 6 weeks, at least about 2 months, at least about 3 months, at least about 6 months, or at least about 1 year.

In certain embodiments, one or more preparations of different probiotic bacteria having modified metabolism can be administered simultaneously (including administering bacteria of the same species or genus, or different species or genus) or sequentially (including administering at different times). Such probiotic bacteria can be prepared from bacteria isolated from microbiota and then grown in a culture using known techniques to develop a modified metabolism. In certain embodiments, bacteria species, for example and not by way of limitation, *Rothia nasimurium* and/or *Escherichia coli* can be administered orally at, for example and not by way of limitation at $10^7$ CFU.

In certain embodiments, the probiotic composition further comprises one or more anti-obesity agent selected from the group consisting of an agent, a therapy, and a pharmaceutically active ingredient that is capable of negatively affecting obesity or weight gain in a subject, for example, by altering one of the fundamental metabolic processes of the host subject's body, as opposed to the probiotic bacteria that themselves have one or more modified fundamental metabolic processes.

In certain embodiments, the second pharmaceutically active ingredient can be an anti-obesity agent. Non-limiting examples of anti-obesity pharmaceutical agents include catecholamine release agents, such as amphetamine, Phentermine™ and related substituted amphetamines (e.g. bupropion), agents that increase the human body's metabolism, agents that interfere with the human body's ability to absorb specific nutrients in food, for example and not by way of limitation, Orlistat® (tetrahydrolipstatin), loscaserin, sibutramine, rimonabant, Metformin™ (N,N-dimethylbiguanide), exenatide, phentermine, as well as herbal and dietary supplements.

In certain embodiments, the probiotic composition can be administered in combination with at least one anti-obesity agent.

"In combination with," as used herein, means that the probiotic composition and the one or more anti-obesity agents are administered to a subject as part of a treatment regimen or plan. In certain embodiments, being used in combination does not require that the probiotic composition and the one or more anti-obesity agent are physically combined prior to administration or that they be administered over the same time frame. For example, and not by way of limitation, the probiotic composition and the one or more anti-obesity agent can be administered concurrently to the subject being treated or can be administered at the same time or sequentially in any order or at different points in time.

In certain embodiments, the present disclosure provides probiotic compositions comprising probiotic bacteria having modified metabolism wherein the probiotic bacteria having modified metabolism are at a concentration of between about 1 weight % and about 100 weight % (% w/w) of the probiotic compositions. In certain embodiments, the probiotic bacteria having modified metabolism are at a concentration of between about 1 ppm and about 100,000 ppm of the probiotic compositions. In certain embodiments, the probiotic bacteria having modified metabolism are at a concentration of about 1 pM of the probiotic compositions.

In certain embodiments, the development of personalized probiotic bacteria having modified metabolism, such as the probiotic bacteria disclosed herein, can allow the use of lower therapeutic amounts due to higher metabolic activity and can further allow the subject to avoid any potential harmful side-effects associated with reintroduction of specific bacterial strains. In certain embodiments, probiotic bacteria having modified metabolism are administered to a different subject. In certain embodiments, probiotic bacteria having modified metabolism are administered to the same subject. In certain embodiments, the bacteria having modified metabolism administered to the same subject have higher capability of colonizing the intestinal mucosa because of bacteria has already been a part of the gut environment, and immune system recognizes these bacteria as part of the microbiome.

5.3 Methods of Use

In another aspect, the presently disclosed matter relates to methods for treating an overweight subject, an obese subject, a subject aiming to maintain their body weight, a subject having normal BMI, or a subject otherwise in need of such treatment. In certain embodiments, the methods comprise administering one or more probiotic compositions comprising probiotic bacteria having modified metabolism, disclosed herein.

In certain embodiments, the methods disclosed herein comprise obtaining a microbiota sample from the subject, isolating bacteria from the microbiota sample, developing probiotic bacteria having modified metabolism by subjecting the isolated bacteria to a stress-based directed evolution; and administering to the subject an effective amount of the probiotic bacteria having modified metabolism.

In certain embodiments, the methods disclosed herein comprise obtaining a microbiota sample from the subject, isolating bacteria from the microbiota sample, selecting probiotic bacteria having modified metabolism from the isolated bacteria, culturing the probiotic bacteria to obtain an effective amount of the probiotic bacteria, and administering to the subject an effective amount of the probiotic bacteria having modified metabolism.

In certain embodiments, the methods disclosed herein comprise obtaining a microbiota sample from the subject, isolating bacteria from the microbiota sample, subjecting the isolated bacteria to a stress-based directed evolution to develop probiotic bacteria that have increased metabolism as compared to the isolated bacteria that are not subject to the stress-based directed evolution, and administering to the subject an effective amount of the probiotic bacteria having increased metabolism.

In certain embodiments, the methods disclosed herein comprise obtaining a microbiota sample from the subject, isolating bacteria from the microbiota sample, selecting probiotic bacteria having modified metabolism from the isolated bacteria, culturing the probiotic bacteria to obtain an effective amount of the probiotic bacteria, and administering to the subject the effective amount of the probiotic bacteria having modified metabolism.

In certain embodiments, the presently disclosed matter relates to methods of inhibiting or reducing the lipid absorption in the gastrointestinal tract of a subject comprising obtaining a microbiota sample from a subject, isolating bacteria from the microbiota sample, developing probiotic bacteria having modified metabolism by subjecting the isolated bacteria to stress-based directed evolution, and administering to the subject an effective amount of the probiotic bacteria having modified metabolism to inhibit or reduce the lipid content that is available for absorption in the gastrointestinal tract of the subject.

In certain embodiments, the microbiota sample is a saliva sample. In certain embodiments, the microbiota sample is a stool sample.

In certain embodiments, the methods disclosed herein comprise administrating to the subject an effective amount of a probiotic composition. In certain embodiments, the probiotic composition comprises probiotic bacteria having lipid metabolism. In certain embodiments, the probiotic composition comprises probiotic bacteria having modified lipid metabolism. In certain embodiments, the probiotic composition comprises probiotic bacteria having increased lipid metabolism, compared to bacteria not subject to stress-based directed evolution. In certain embodiments, the probiotic composition comprises probiotic bacteria having fatty acid metabolism. In certain embodiments, the probiotic composition comprises probiotic bacteria having modified fatty acid metabolism. In certain embodiments, the probiotic composition comprises probiotic bacteria having increased fatty acid metabolism, compared to bacteria not subjected to stress-based directed evolution. In certain embodiments, the probiotic composition comprises probiotic bacteria having modified lipase activity or other enzymes involved in lipid metabolism. In certain embodiments, the probiotic composition comprises probiotic bacteria having increased lipase expression, compared to bacteria not subject to stress-based directed evolution. In certain embodiments, the probiotic bacteria having modified metabolism prevent lipid absorption by the subject by actively decreasing the amount of lipids available for absorption by the subject.

In certain embodiments, the probiotic bacteria having modified metabolism survive in culture medium having at least about 60%, about 70%, about 80%, about 90%, about 95%, about 99%, or about 100% v/v lipids.

In certain embodiments, the probiotic bacteria having modified metabolism prevent lipid absorption by the subject by actively decreasing the amount of lipids available for absorption by the subject.

In certain embodiments, administering to the subject an effective amount of the probiotic bacteria having modified metabolism results in inhibiting weight gain in the subject and/or reducing body weight in the subject.

In certain embodiments, administering to the subject an effective amount of the probiotic bacteria having modified metabolism results in maintaining a normal BMI of a subject.

In certain embodiments, the probiotic bacteria having modified metabolism are administered to the same subject from whom the probiotic bacteria are derived. In certain embodiments, the probiotic bacteria having modified metabolism are administered to a different subject from whom the probiotic bacteria are derived.

In certain embodiments, the presently disclosed matter is directed to kits comprising an effective amount of a probiotic composition disclosed herein.

In certain embodiments, provided herein is a method of treating an overweight, an obese subject, a subject aiming to maintain their body weight and/or a normal BMI, or a subject otherwise in need of such treatment by administering orally a probiotic composition disclosed herein, wherein the probiotic composition comprises probiotic bacteria having modified metabolism, thereby decreasing quantities of energy molecules in the gastrointestinal (GI) tract when administered to a subject, thus decreasing absorption by the subject.

In certain embodiments, a subject provides a swab sample from the mouth. This sample is processed to isolate bacteria. The isolated bacteria are cultured in vitro and probiotic bacteria are selected from the isolated bacteria for the specific trait of having highly active lipid metabolism. The probiotic bacteria that specifically utilize large levels of fatty acid oxidation are isolated, grown in vitro, and are developed into a formulation. This formulation is then given to the subject, to be taken daily or alternate days, so as to increase the number of probiotic bacteria that metabolize or store lipids in the gastrointestinal tract of the subject. The probiotic bacteria having modified lipid metabolism decrease the amount of lipids available for absorption by the subject, thereby decreasing the amount of lipids absorbed systemically through the intestines, and thus prevent weight gain in the subject.

In certain embodiments, lipid metabolism refers to fatty acid oxidation mediated energy generation and/or lipogenesis.

In certain embodiments, provided herein are methods for treating an overweight or obese subject by administering one or more probiotic compositions disclosed herein comprising one or more probiotic bacteria species, strain, or genus having modified metabolism. In certain embodiments, the treatment can include administration of at least one of probiotic bacteria species or genus included in Table 1 and bacteria species or genus disclosed herein.

In certain embodiments, provided herein are methods for treating an overweight, an obese subject, a subject aiming to maintain their body weight and/or a normal BMI, or a subject otherwise in need of such treatment by administering one or more probiotic compositions disclosed herein comprising one or more probiotic bacteria species, strain, or genus having modified metabolism in combination with at least one anti-obesity agent. In certain embodiments, treatment of an overweight or obese subject can also include one or more conventional regimens including, for example, bariatric surgery.

In certain embodiments, provided herein are methods for treating various diseases associated with obesity, for example and not by way of limitation, type 2 diabetes, cardiovascular, hypertension, stroke and certain forms of cancer, by administering the probiotic compositions disclosed herein.

In certain embodiments, provided herein are methods for treating metabolic conditions, by administering the probiotic compositions disclosed herein. In certain embodiments, metabolic conditions such as, for example, a disorder of fatty acid oxidation, steroid metabolism (e.g., congenital adrenal hyperplasia), abnormal lipid metabolism, and metabolic depletion of molecules in the gastrointestinal tract, for example and not by way of limitation cholesterol and allergy causing molecules.

In certain embodiments, the probiotic compositions described herein can be administered in combination with other therapeutic agents or regimes. The choice of therapeutic agents that can be co-administered with the bacterial compositions depends, in part, on the condition being treated.

In certain embodiments, the probiotic bacteria-based treatment regimen can be further supplemented by a dietary change. In certain embodiments, the dietary change includes decreasing dietary fat and/or increasing fiber consumption. In certain embodiments, the dietary change further includes switching from a modified fat diet to a low-fat diet. In certain embodiments, the dietary change is a switch from a modified lipid diet to a low lipid diet. In certain embodiments, the probiotic bacteria based treatment regimen can be further supplemented by exercise.

5.4 Kits

In non-limiting embodiments, the presently disclosed subject matter provides a kit for administering a probiotic composition of the presently disclosed subject matter. In certain embodiments, the kit comprises an effective amount of one or more probiotic bacteria species, strain, or genus subject to stress-based directed evolution or a probiotic composition as described above. In certain embodiments, the kit comprises a probiotic composition comprising an effective amount of one or more probiotic bacteria species, strain, or genus subject to stress-based directed evolution. In certain embodiments, the kit comprises an effective amount of probiotic bacteria having modified metabolism or a probiotic composition comprising probiotic bacteria having modified metabolism as disclosed herein.

In certain embodiments, the kit can further include one or more components such as instructions for use, devices and additional reagents, and components, such as tubes, containers and syringes for performing the methods disclosed above. In certain embodiments, the kit can further include one or more agents, e.g., anti-obesity agents, that can be administered in combination with a probiotic composition.

In certain embodiments, the kit can include instructions for use, a device for administering the probiotic composition to a subject, or a device for administering an additional agent or compound to a subject. For example, and not by way of limitation, the instructions can include a description of the probiotic composition and, optionally, other components included in the kit, and methods for administration, including methods for determining the proper state of the subject, the proper dosage amount, the proper administration method of administering the probiotic composition, and/or the proper storage of the kit. Instructions can also include guidance for monitoring the subject over the duration of the treatment time.

In certain embodiments, the kit can include a device for administering the probiotic composition and/or one or more agents, e.g., anti-obesity agents to a subject. Any of a variety of devices known in the art for administering medications and probiotic compositions can be included in the kits provided herein. Non-limiting examples of such devices include, a hypodermic needle, an intravenous needle, a catheter, a needle-less injection device, an inhaler and a liquid dispenser, such as an eyedropper. In certain embodiments, a probiotic composition and/or one or more agents, e.g., anti-obesity agents to a subject to be delivered systemically, for example, by intravenous injection, can be included in a kit with a hypodermic needle and syringe.

In certain embodiments, the kit can comprise one or more containers containing a probiotic composition, disclosed herein. For example, and not by way of limitation, the kit can comprise one or more containers that contain probiotic bacteria comprising at one or more bacteria species, strain, or genus subject to stress-based directed evolution and/or a probiotic composition comprising probiotic bacteria having modified metabolism or a portion thereof.

6. EXAMPLES

The following Examples are offered to more fully illustrate the disclosure, but are not to be construed as limiting the scope thereof.

Example 1: Probiotics of the Disclosed Subject Matter have Higher Lipase Activity as Compared to Freshly Isolated Probiotics Isolation and Stress-Based Directed Evolution of Probiotics in Mouse Saliva.

To determine if stress-based directed evolution using stressors can modulate the lipase function of probiotics, probiotics from saliva of C57BL6/J mice were isolated and cultured in increasing levels of lipids. These isolated bacteria were then cultured on Spirit blue agar plate overnight. The spirit blue agar was generated by utilizing autoclaving spirit blue and later adding 0.3% Tween®80 or soy bean oil as the lipid source of energy. The bacteria that grew on the plates generated a halo on the agar were considered to be positive for lipase activity. A 15% glycerol stock of these bacteria (grown overnight in LB broth) was frozen in −80° C. and considered to be a passage 0 or freshly isolated bacteria. Next a stab from this frozen stock was grown overnight in the presence of 2% Tween® 80 (stock of Tween®80=1% Tween®80 in PBS) and 98% LB broth.

The stab can be obtained using a sterile pipette tip. The only other source of energy besides lipids was through the growth medium provided through LB broth.

A 100 µL of the bacteria that grew overnight was then added to 10% tween 80 and 90% LB broth and further cultured overnight. This procedure of growing probiotics in increasing levels of soybean oil or Tween®80 (10%, 20%, 40%, 80%, 100%) was performed.

In order to determine if the lipase activity was enhanced due to the increased stress, frozen stock at different stressor stages were tested using a colorimetric lipase activity test. These cells were also plated on LB agar plates to determine CFUs. The data obtained from the lipase activity was reported as Units/liter/CFU. It was determined the lipase activity of probiotics cultured in 100% Tween® 80 solution was 1.1 to 3-fold higher than freshly isolated probiotics. On the other hand, the probiotics that did not generate halo on spirit blue agar (low lipase activity) had substantially lower lipase activity (FIG. 5).

Isolation and Stress-Based Directed Evolution of Probiotics in Human Saliva

To isolate probiotics from human saliva for purposes of stress-based directed evolution, a pooled normal (non-diseased) human saliva sample is purchased and processed at Evolved Probiotics Inc. (FIG. 6). The human saliva is thawed (shipped frozen), homogenized, centrifuged and washed with phosphate buffered saline (2500×Gs for 5 min three times) to isolate bacteria. These bacteria are then plated on Difco© spirit blue agar plates (diluted $10^1$, $10^3$, $10^4$, $10^5$) to isolate individual colonies of lipolytic bacteria. Representative colonies (total of five) are isolated and stress-based directed evolution via lipid stress environment is carried out as detailed in FIG. 4. The lipase activity is tested using lipase detection kit and the ability of the bacteria to survive in 100% lipid environment is evaluated. These five bacteria are then optionally genetically identified using MALDI-TOF microbial or 16S ribosomal RNA (rRNA) genotyping.

Probiotics from human saliva are isolated and stress-based directed evolution on the probiotics isolated from human saliva is performed. If multiple species of microbial flora (e.g. Fungi) are isolated, saliva is first centrifuged at 300×Gs to remove fungi and then centrifuged at 2500×Gs to isolate bacteria. If the lipase activity is not increasing or if the bacteria are not able to survive in 100% Tween™80 solution in PBS, then the percentage of lipid is increased 10% at a time (ex. 10%, 20%, 30%) to acclimatize the bacteria to lipid environment. Furthermore, five more bacterial colonies are isolated from initial plate if the above method is not successful, and the stress-based directed evolution is performed on these new set of bacteria. This process continues until at least one bacteria is isolated which can survive in 100% lipid environment.

Example 2: Probiotics of the Disclosed Subject Matter can Colonize the GI Tract of Littermates from which they were Isolated at Higher Levels than a Different Strain of Mice To determine if the probiotic bacteria isolated from the littermates (mice from the same cage) can colonize the GI tract in these same littermates better than non-littermate mice, probiotics were isolated, cultured and delivery through gavage to litter-mate and non-littermate mice. Specifically, probiotics were isolated from the mouth of the mice using a Q-tip®. It is important not to mix mice (or isolated bacteria) from different cages because mice are coprophagic, and as a result, littermates from the same cage essentially have the same microbiome, which can be vastly different than littermates in a different cage. These probiotics bacteria were then grown on a spirit blue agar plate and a colony with lipase activity was isolated (FIG. 7A). These probiotic bacteria were then transformed using a red-fluorescent-protein (RFP) plasmid as a reporter gene. Next the probiotic bacteria were grown in LB broth and re-administered to the mice (C57BL/6J littermates and BALB/c mice) using oral gavage, After 24 hours post-gavage, stomach, duodenum, ileum, jejunum, and cecum of mice were isolated. These tissues were then stained for nucleus and mounted on slides. The images (FIG. 7B) were then analyzed using a fluorescent microscope. As shown in FIG. 7B, the probiotic bacteria colonized in the same littermates from which the bacteria were isolated. Furthermore, it was observed that these bacteria colonized throughout the GI tract, but in higher numbers in duodenum, jejunum and cecum. Overall, these data showed that the isolated probiotics from saliva preferentially colonized in the same littermates that they were isolated from, rather than in the BALB/c mice that were not littermates (did not share the cage with C57BL/6J mice), and thus might have different microbiota.

Example 3: Oral Gavage of Probiotics of the Disclosed Subject Matter in the Presence of High-Fat Diet Prevents Weight Gain, and in Conjunction with Diet-Change Led to Weight Loss in Mice To determine if the probiotics of the disclosed subject matter can lead to prevention of weight gain or lead to weight loss in pre-clinical mouse models, a diet-induced-obesity (DIO) model of C57BL6/J mice (on high-fat diet (HFD)-60% of Kcal coming from fat) was utilized. Probiotic bacteria were isolated and subject to stress-based directed evolution in accordance with the methods disclosed in Example 1. For prevention of weight gain studies, age-matched mice (6-8 weeks, equal number of males and females) were fed with HFD (for 50 days) along with alternate day of oral gavage of either the probiotic bacteria or non-evolved bacteria DH5α (start at day 30; CFU=$10^7$/50 µL of saline per mouse). Weight changes in mice were recorded and plotted (FIG. 8A). FIG. 8A shows that the mice that were orally gavaged with probiotics of the disclosed subject matter gained weight much slower than the mice that were fed with DH5α in the presence of HFD. It was observed that the mice that received HFD and control bacteria DH5α had shinier fur as compared to the mice that received the presently disclosed probiotics (FIG. 9). Moreover, the overall size of the mice receiving control bacteria DH5α was much larger than the mice receiving the presently disclosed probiotics. Without being limited to any particular theory, these data show that the probiotics of the disclosed subject matter were able to prevent the lipid absorption.

For weight loss studies, age-matched mice (6-8 weeks, males) were fed HFD for 1 month. Next, diet was switched to regular chow (% 12 Kcal of fat) and mice were either provided with probiotics or DH5α (CFU=$10^7$/50 µL of saline) every alternate day for 30 days. The change in weight over a period of 8 days was noted and plotted (FIG. 8B). These data show that the reduction in fat consumption in the presence of probiotics of the disclosed subject matter led to dramatic decrease in weight as compared to the mice that were given DH5α. These data further show that the probiotics of the disclosed subject matter can directly modulate the amount of fat absorbed in the body.

Another experiment where mice were provided with either high-fat diet or normal chow. These mice were then treated with either saline or probiotics every alternate day. The weight gain was determined. FIG. 10A shows the change of weight over the period of the experiment. FIG. 10B is a representative image of mice that are provided with high-fat diet and treated with saline and provided with high-fat diet and treated with the probiotics. The fur of mice that are treated with saline was "ruffled," whereas the fur of the mice treated with probiotics was normal. Without being bound to any particular theory, this shows that the mice consuming smaller amounts of probiotics actually absorbed lesser amount of fat. Furthermore, the size of the mice treated with saline was larger than the mice treated with probiotics.

In summary, preliminary data demonstrated that by administering modified probiotics (that have undergone stress-based, directed evolution to develop modified lipid metabolism in the intestines) can reduce weight gain and lead to weight loss when combined with diet change. These probiotics were originally isolated from saliva of a diet-induced obesity mouse model, and then, following stress-based directed evolution, survive entirely on metabolism of lipid molecules. These probiotics, when administered to mice via oral gavage in the presence of high-fat diet led to reduced weight gain. Moreover, changing the diet from high-fat to regular chow in the presence of probiotics of the disclosed subject matter, led to a 2× weight loss compared to the control of non-evolved bacteria that were provided with regular chow.

Example 4: Develop a Solid Oral Dosage Formulation for Probiotics of the Disclosed Subject Matter and Test its Efficacy Post-Formulation in Mice To generate pills containing probiotics of the disclosed subject matter and test its efficacy in weight-loss in the presence of diet change, the ability of probiotics of the disclosed subject matter to reduce weight in DIO mouse model (used in Example 3) when HFD fed mice are orally gavaged with probiotics of the disclosed subject matter in pill format in the presence of diet change is evaluated. Specifically, bacteria are isolated from mice and stress-based directed evolution is performed on these bacteria as described in Example 2. These bacteria are then harvested by centrifugation at 4,000 g for 25 min at 4° C. The cell mass is then mixed with sterile 15% glycerin made in PBS in a ratio 1:5 (1 mL of glycerin for 5 g of pelleted cells).[6] After freeze-drying procedure, the viability, lipase activity, ability to consume lipids as energy source is analyzed. The ability to consume lipids in the environment typically observed in the duodenum and jejunum is also tested and analyzed. Next, empty pills for mice are utilized and filled with probiotics of the disclosed subject matter representing $10^7$ CFU.

Mice are fed HFD ad libitum for 2 months. These mice are then switched to regular chow and orally gavaged with pill containing $10^7$ CFU of evolved probiotics (alternate day for 2 months) and the weight is observed for 2 months. The probiotics of the disclosed subject matter delivered in the form of a pill conjunction with reduced fat diet, induce a more rapid and robust weight loss that no probiotic control in mice. In certain embodiments, the CFU of probiotics are increased to $10^8$, $10^9$, or $10^{10}$ in the pills and the weight-loss experiments are performed again.

In certain embodiments, pills are orally gavaged to HFD fed mice for 1 month (instead of 2 months) in order to test the effect on over-weight mice, instead of obese mice. If the pills create an issue as far as delivery of probiotics of the disclosed subject matter to the lower GI tract, or causing discomfort in mice, solid dosages in the form of tablets are developed by mixing probiotics of the disclosed subject matter with sodium alginate, calcium carbonate, glyceryl monooleate, triethyl citrate, and acetylated monoglyceride, and hypromellose acetate succinate (HPMCAS).[7-9]

In certain embodiments, an oral dosage form with $10^9$ and $10^{10}$ CFUs (generally used in probiotic products) of probiotics of the disclosed subject matter isolated from mice that are susceptible to diet-induced obesity are performed. These pills undergo dissolution testing in a standardized, USP II Dissolution Apparatus using pH=6.8 phosphate buffer (simulated intestinal fluid) and also simulated gastric fluid. The ability of the probiotics of the disclosed subject matter to prevent weight gain in C57BL/6J mice is determined by providing mice the pills and high-fat diet (60% Kcal of fat) and monitoring the weight gain over a period of 1 month. Furthermore, experiments to monitor weight loss in C57BL/6J mice are performed (high-fat diet fed for 1 month) along with or without change in diet (regular chow-12% Kcal of fat). Finally, organs and blood are isolated from mice post-administration and are evaluated for metabolic outputs, such as blood glucose levels (among others).

Moreover, the survival and activity of probiotics of the disclosed subject matter in the harsh environment of the intestines is tested using simulated gastric fluid in vitro. A genetic analysis of the isolated bacteria is also performed (MALDI-TOF/16S ribosomal RNA (rRNA) genotyping), in order to identify lineage and the susceptibility of these bacteria to different antibiotics and to determine pathogenicity.

Example 5: Presently Disclosed Probiotics Do Not Modulate Host Metabolism as Evaluated by Energy Expenditure (EE) Adjusted for Lean Mass, Total Movement, Food and Water Intake at Thermoneutrality To determine if the energy expenditure (a measure of metabolism of the host) is influenced by the presently disclosed probiotics, C57BL/6j mice were fed high fat diet (HFD) or regular diet (RD), and were given either probiotic bacteria or DH5α every alternate day for 14 days (CFU=$10^7$/ 50 μL of saline per mouse) (FIG. 11A). The probiotic bacteria administered to the mice were isolated and underwent stress-based directed evolution in accordance with the method disclosed in Example 3. The mice were then transferred to metabolic cage and were kept on HFD for 96 hours. Experiments were performed at a constant 30° C. (thermoneutrality for mice) for the entire 96 hours. Thermoneutrality was chosen for this experiment to ensure that the EE differences between the groups that were observed was mainly due to the probiotics administration. Once in the metabolic chamber, total movement, food intake, water intake, $VO_2$, $VCO_2$, and weight were determined every 5 min.

It was observed that the EE adjusted for lean mass using analysis of covariance (ANCOVA) were not significantly different from each other in Probiotics+HFD vs. DH5α+HFD: Probiotics+RD vs. DH5α+RD for the first 2 days (FIG. 11B). Interestingly, the total movement between the Probiotics+HFD and DH5α+HFD was significantly different from each other for the first 48 hours, however this difference was not significantly different after 48 hours (FIG. 11C, data shown only for first 24 hours). These data suggest that the effect of probiotic bacteria on the movement of mice is only for the first 48 hours, after which another administration of the probiotics may be required to maintain the effect. Moreover, the food intake (FIG. 11D) and water intake (data not shown) between the groups of mice getting the same chow (HFD or RD) were not significantly different, which strongly suggests important health measures are unchanged by probiotic bacteria administration. Lastly, the weight of the mice at the last time point was compared for different groups (FIG. 11E). It was observed that the total weight of mice was significantly lower in Probiotics+HFD vs. DH5α+HFD. Moreover, this difference accounted for 2 to 4 g (or 10% to 20% of the body weight), which has significant implications for preventing weight gain in larger animal models and humans.

Overall, these results suggest that the presently disclosed probiotics do not modulate the metabolism of the host and appear to not influence the animals in eating, drinking and moving normally.

Example 6: Fat Mass, but not the Lean Mass, is Significantly Lower in Probiotics+HFD Group To determine if the change in the weight observed in Example 5 was due to decrease in fat or lean mass or both, after the metabolic cage experiment performed in Example 5, Echo-MRI DXA studies were performed. It was observed that there were no significant differences in fat mass between Probiotics+HFD, Probiotics+RD, and DH5α+RD; and these three were significantly lower than DH5α+HFD (FIG. 12). These results suggest that the difference in weight gain was due to fat mass, which supports that the probiotics are preventing the transport of fat through the intestines and deposition in the body.

Example 7: Triglyceride Levels after Fat Gavage, and Fatty Acid Content was Significantly Lowered in Serum by the Probiotics as Compared to Control Bacteria To determine if the presently disclosed probiotics decrease the fatty acid content in the blood of mice (responsible for cardiovascular disorders among other complications), after performing the Echo MRI DAX studies as disclosed in Example 6, mice were bled and euthanized.

Serum was separated from blood and commercial assay kits for determining total fatty acid content was utilized. It was observed that the total fatty acid content was significantly higher in DH5α+HFD group as compared to all the other groups (FIG. 13A). These data suggest that the probiotics actively prevented fatty acid build up in the blood, even though these mice were fed HFD.

To determine if the probiotics disclosed herein can in real-time decrease the triglyceride levels (indicative of the lipids absorbed through the gut in mice as they are fed fats), mice were orally gavaged with soybean oil with either the probiotics or DH5a. The mice were then bled every hour, serum was separated from the blood and the amount of triglyceride in the serum was determined using a commercial assay kit. It was observed that the probiotics were able to prevent the increase in triglycerides in the serum as compared to control bacteria (FIG. 13B). These results support that the probiotics can prevent the transport of lipids through the intestines.

Example 8: The Measurement of Intestinal Fat Absorption Shows that the Presently Disclosed Probiotics Store/Consume Lipids To determine if the mice are able to remove fat consumed through chow, HFD containing non-absorbable behenic acid (standard) was provided to mice along with alternate day of the probiotics or DH5α oral gavage (FIG. 14A). The probiotics administered to the mice were isolated and underwent stress-based directed evolution in accordance with the method disclosed in Example 3. The stool samples from mice were collected and analyzed using mass-spectroscopy to determine the type and amount of lipids in the stool. It was observed that the mice receiving the probiotics excreted significantly higher (1.6 fold higher-FIG. 9B) fat in the stool. Specifically, oleic acid (major component of the fat mass in adipose tissue)37,38 was determined to be excreted in significantly higher quantities in the probiotics group as compared to DH5α group (FIG. 9C). These results suggest that the probiotics are able to prevent the absorption of the lipids through the gut, some of which are then excreted in the stool.

In summary, the presently disclosed probiotics are highly efficient at preventing weight gain in mice even though mice consume HFD, and also that weight loss is more efficient when the probiotics are combined with diet change. This change in weight can be attributed to the evolved probiotic bacteria storing/consuming the lipids inside the bacteria (FIG. 16—proposed mechanism of action). Lastly, the probiotics do not change the metabolism of the host or lead to abnormal food and water intake and movement, supporting that lipids are being stored or metabolized by the evolved, personalized probiotic as opposed to being absorbed in the host.

Example 9: The Presently Disclosed Probiotics Modulated the Lipids in the Supernatant as Determine by Mass-Spectroscopy In Vitro In order to test if the probiotics disclosed herein are able to modulate the lipids present in the growth media, stress-based directed evolution was performed on bacteria isolated from the saliva of mice. These bacteria were then cultured in lipid-rich medium consisting of 40% LB broth (essential for obtaining a good yield of bacteria), 40% soy bean oil (as the lipid source), and 10% Tween® 20 (as an emulsifier to ensure mixing of the oil and LB broth medium). Controls included bacteria that did not undergo stress-based directed evolution cultured in lipid-rich medium, and lipid-rich medium by itself. After culturing for 16 hours at 37 C at 200 rpm, supernatant and bacteria were separated. Lipid extraction and methylation was performed to isolate the lipids, 44 and GC-MS and NIST library were utilized to identify the lipids. The analysis suggested some of the lipids (specially for early elution time) were decreased in the supernatant in the presence of the probiotics. Moreover, new lipids were observed (later elution time) in probiotics' supernatant (data not shown). Moreover, for same CFU, higher number of lipids were found in the probiotic bacteria as compared to the control bacteria (FIG. 17—analysis, dark gray-no lipids, light gray-presence of lipids). These results suggest that the stress-based directed evolution process can be utilized to modulate the intracellular lipid content of the bacteria.

Example 10: Probiotics can be Isolated from Saliva of Dogs and Identified Using 16s rDNA Dog saliva (one dog) was obtained and the presently disclosed probiotics from the dog saliva was generated. Specifically, dog saliva was obtained by swabbing a golden retriever male dog, and the Q-tip® was stored at 4 C until used. The saliva was then extracted, diluted (10 fold, 7 times) and spread on a Spirit Blue agar plate with 0.3% soy bean oil as the source of oil. The colonies (a total of 4) that generated a halo on the plate were then picked, cultured in LB broth and 16s rDNA was utilized to identify the species of the bacteria. A representative Neighbor Joining Tree plot is shown in FIG. 15. The most common species that survived and grew (largest colonies) were identified to be *Staphylococcus delphini, Staphylococcus intermedius* and *Staphylococcus* pseudintermedius. Dogs are the natural host of these species of bacteria. Moreover, these species of bacteria are important canine commensal and opportunistic pathogen in dogs, but largely benign for humans.

Example 11: Probiotics can be Isolated from Saliva of Humans and Identified Using 16s rDNA Human saliva was obtained, and the presently disclosed probiotics were generated from the saliva. Specifically, saliva was obtained by swabbing a male human, and the Q-tip® was stored at 4° C. until used. The saliva was then extracted, diluted (10 fold, 7 times) and spread on a Spirit Blue agar plate with 0.3% soy bean oil as the source of oil. The colonies (a total of 4) that generated a halo on the plate were then picked, cultured in LB broth and 16s rDNA was utilized to identify the species of the bacteria. A representative Neighbor Joining Tree plot is shown in FIG. 18. The most common species that survived and grew (largest colonies) was identified to be *Streptococcus salivarius*. Notably, *Streptococcus salivarius* is one of the first colonizers of the human oral cavity and gut after birth and is known to prevent pathogen bacteria from colonizing. These data suggest that benign bacteria can be isolated form the saliva of humans, expanded ex vivo, and identified for performing stress-based directed evolution.

7. REFERENCES

1. Ng, M. et al. Global, regional, and national prevalence of overweight and obesity in children and adults during 1980-2013: A systematic analysis for the Global Burden of Disease Study 2013. Lancet 384(9945): 766-81 (2014).

2. Lim, S. S. et al. A comparative risk assessment of burden of disease and injury attributable to 67 risk factors and risk factor clusters in 21 regions, 1990-2010: A systematic analysis for the Global Burden of Disease Study 2010. Lancet 380(9859):2224-60 (2012).
3. Flegal, K. M., Carroll, M. D., Ogden, C. L. & Curtin, L. R. Prevalence and trends in obesity among US adults, 1999-2008. JAMA 303(3):235-41 (2010).
4. Yatsunenko, T. et al. Human gut microbiome viewed across age and geography. Nature 486(7402):222-7.
5. Kau, A. L., Ahern, P. P., Griffin, N. W., Goodman, A. L. & Gordon, J. I. Human nutrition, the gut microbiome and the immune system. Nature 474(7351):327-36 (2011).
6. Savini, M. et al. Pilot-scale production and viability analysis of freeze-dried probiotic bacteria using different protective agents. Nutrients 2(3):330-9 (2010).
7. Park, H. J., Lee, G. H., Jun, J., Son, M. & Kang, M. J. Multiple-unit tablet of probiotic bacteria for improved storage stability, acid tolerability, and in vivo intestinal protective effect. Drug Des. Devel. Ther. 10:1355-64 (2016).
8. Ding, W. K. & Shah, N. P. An improved method of microencapsulation of probiotic bacteria for their stability in acidic and bile conditions during storage. J. Food Sci. 74(2):M53-61 (2009).
9. Ding, W. K. & Shah, N. P. Effect of various encapsulating materials on the stability of probiotic bacteria. J. Food Sci. 74(2):M100-7 (2009).
10. Hamad, E. M. et al. Milk fermented by *Lactobacillus gasseri* SBT2055 influences adipocyte size via inhibition of dietary fat absorption in Zucker rats. Br. J. Nutr. 101(5): 716-24 (2009).
11. Kang, J. H. et al. Anti-Obesity Effect of *Lactobacillus gasseri* BNR17 in High-Sucrose Diet-Induced Obese Mice. PLOS One 8(1):e54617 (2013).
12. Jung, S.-P. et al. Effect of *Lactobacillus gasseri* BNR17 on Overweight and Obese Adults: A Randomized, Double-Blind Clinical Trial. Korean J. Fam. Med. 34(2): 80-9 (2013).
13. H. Borgeraas, L. K. Johnson, J. Skattebu, J. K. Hertel, J. Hjelmesaeth, Effects of probiotics on body weight, body mass index, fat mass and fat percentage in subjects with overweight or obesity: a systematic review and meta-analysis of randomized controlled trials. Obes Rev. 19(2): 219-232 (2018).
14. Semova I, Carten J D, Stombaugh J, Mackey L C, Knight R, Farber S A, Rawls J F. Microbiota regulate intestinal absorption and metabolism of fatty acids in the zebrafish. Cell Host Microbe. 12(3):277-288 (2012).
15. Lee S M, Donaldson G P, Mikulski Z, Boyajian S, Ley K, Mazmanian S K. Bacterial colonization factors control specificity and stability of the gut microbiota. Nature. September 19:501(7467):426-9 (2013).
16. Phalipon A, Cardona A, Kraehenbuhl J P, Edelman L, Sansonetti P J, Corthésy B. Secretory component: a new role in secretory IgA-mediated immune exclusion in vivo. Immunity. July:17(1): 107-15 (2002).

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various patents and patent applications are cited herein, the contents of which are hereby incorporated by reference herein in their entireties.

What is claimed is:

1. A method of making a probiotic composition comprising:
    (a) obtaining a saliva sample or a stool sample from a mammalian subject;
    (b) isolating bacteria from the saliva or the stool sample;
    (c) subjecting the isolated bacteria to a stress-based directed evolution to generate probiotic bacteria therefrom, wherein the stress-based directed evolution comprises culturing the bacteria in increasing lipid concentrations, wherein the probiotic bacteria have an increased fatty acid metabolism and/or increased lipase activity as compared to the bacteria not subjected to the stress-based directed evolution; and
    (d) incorporating the probiotic bacteria to a composition to produce the probiotic composition.

2. The method of claim 1, wherein the subject is a human subject.

3. The method of claim 1, wherein the subject is overweight or obese.

4. The method of claim 1, wherein the probiotic bacteria survive in culture media comprising at least about 60% v/v lipids.

5. The method of claim 1, wherein the probiotic bacteria utilize lipids as a source of energy.

6. The method of claim 1, further comprising growing the probiotic bacteria to obtain an effective amount of the probiotic bacteria.

7. The method of claim 1, further comprising genetically identifying the probiotic bacteria.

8. The method of claim 1, wherein the probiotic composition is formulated for administration to said subject.

9. The method of claim 1, wherein the probiotic composition is formulated for oral administration to said subject.

10. The method of claim 8, wherein the probiotic bacteria decrease the amount of lipids that are available for absorption in the gastrointestinal tract of said subject.

11. The method of claim 8, wherein the probiotic bacteria inhibits weight gain in the subject.

12. The method of claim 9, wherein the probiotic composition is in the form of a food additive or a fortified food.

13. The method of claim 9, wherein the probiotic bacteria are mixed with a carrier.

14. The method of claim 9, wherein the probiotic bacteria are applied to liquid or solid food, feed, or drinking water.

15. The method of claim 8, wherein the probiotic composition is formulated for administration as a solution, a tablet, or as a lyophilized culture.

* * * * *